(12) United States Patent
Chilcote et al.

(10) Patent No.: US 7,358,331 B2
(45) Date of Patent: Apr. 15, 2008

(54) TRUNCATED FRAGMENTS OF ALPHA-SYNUCLEIN IN LEWY BODY DISEASE

(75) Inventors: Tamie J Chilcote, San Francisco, CA (US); Jason Goldstein, Doraville, GA (US); John P Anderson, San Francisco, CA (US); Donald Walker, Pleasant Hill, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 240 days.

(21) Appl. No.: 11/194,115

(22) Filed: Jul. 29, 2005

(65) Prior Publication Data

US 2006/0259986 A1 Nov. 16, 2006

Related U.S. Application Data

(63) Continuation-in-part of application No. 10/969,335, filed on Oct. 19, 2004, which is a continuation-in-part of application No. 10/850,570, filed on May 19, 2004, now abandoned, application No. 11/194,115, and a continuation-in-part of application No. PCT/US2004/015836, filed on May 19, 2004.

(60) Provisional application No. 60/471,929, filed on May 19, 2003.

(51) Int. Cl.
C07K 14/00 (2006.01)
C12P 21/06 (2006.01)
C12N 15/00 (2006.01)
A61K 38/00 (2006.01)

(52) U.S. Cl. ............... 530/300; 530/350; 435/69.1; 435/440; 514/2; 514/12

(58) Field of Classification Search ............... 530/300, 530/350; 435/69.1, 440; 514/2, 12
See application file for complete search history.

(56) References Cited

U.S. PATENT DOCUMENTS 5,604,102 A 2/1997 McConlogue et al.
6,780,971 B2 8/2004 Wolozin et al.

FOREIGN PATENT DOCUMENTS

WO WO 00/18917 A2 4/2000
WO WO 00/72876 A2 12/2000
WO WO 2004/041067 A2 5/2004

OTHER PUBLICATIONS

Bennett et al., "Degradatiuon of α-Synuclein by Proteasome," *J. Biol. Chem.*, 274:33855-33858 (1999).
Crowther et al., "Synthetic filaments assembled from C-terminally truncated a-synuclein," *FEBS Letters* 436:309-312 (1998).

Ellis et al., "α-Synuclein Is Phosphorylazed by Members of the Src Family of Protein-tyroaine Kinases," *J. Biol. Chem.*, 276(6):3879-3884 (2001).
Glasson et al., "Mutant and Wild Type Human α-Synucleins Assemble into Elongated Filaments with Distinct Morphologies in Vitro," *J. Biol. Chem.*, 274(12):7619-7622 (1999).
Hamburger et al., "Isolation and characterization of monoclonal antibodies reactive with endothelial cells," *Tissue Cell* 17(4):451-459 (1985) abstract only.
Hoyer et al., "Dependence of alpha-Synuclein Aggregate Morphology on Solution Conditions," *J. Mol. Biol.*, 322:383-393 (2002).
Kim et al., "Structural and functional implications of C-terminal regions of alpha-synuclein," *Biochemistry*, 41(46):13782-13790 (2002).
Kim et al., "Structural Change in Alpha-Synuclein Affect its Chaperone-like Activity In Vitro," *Protein Science*, 9:2489-2496 (2000).
Lee et al., "Formation and Removal of α-Synuclein Aggregates in Cells Exposed to Mitochondrial Inhibitors," *J. Biol. Chem.*, 277(7):5411-5417 (2002).
Mishizen-Eberz et al., "Distinct cleavage patterns of normal and pathologic forms of alpha-synuclein by calpain in vitro," *J. Neurochemistry*, 86(4):836-847 (2003).
Okochi et al., "Constitutive Phosphorylation of the Parkinson's Disease Associated alpha-Synuclein," *J. Biol. Chem.*, 275(1):390-397 (2000).
Takahashi et al., "Phosphorylation of α-synuclein characteristics of synucleinopathy lesions is recapitulated in α-synuclein transgenic Drosophila," *Neuroscience Letters*, 336:156-158 (2003).
Tsim et al., "Monoclonal antibodies specific for the different subunits of asymmetric acetylcholinesterase from chick muscle," *J. Neurochem.*, 51(1):95-104 (1988) abstract only.
Watson et al., "The Introduction of Foreign Genes into Mice," *Molecular Biology of Watson Recombinant DNAs*, 2nd edition, pp. 255-272 (1993).

*Primary Examiner*—Jon Weber
*Assistant Examiner*—Ritra Mitra
(74) *Attorney, Agent, or Firm*—Townsend and Townsend and Crew, LLP

(57) ABSTRACT

The application identifies novel fragments of alpha-synuclein in patients with Lewy Body Disease (LBD) and transgenic animal models thereof. These diseases are characterized by aggregations of alpha-synuclein. The fragments have a truncated C-terminus relative to full-length alpha-synuclein. Some fragments are characterized by a molecular weight of about 12 kDa as determined by SDS gel electrophoresis in tricine buffer and a truncation of at least ten contiguous amino acids from the C-terminus of natural alpha-synuclein. The site of cleavage preferably occurs after residue 117 and before residue 126 of natural alpha-synuclein. The identification of these novel fragments of alpha-synuclein has a number of application in for example, drug discovery, diagnostics, therapeutics, and transgenic animals.

11 Claims, 18 Drawing Sheets

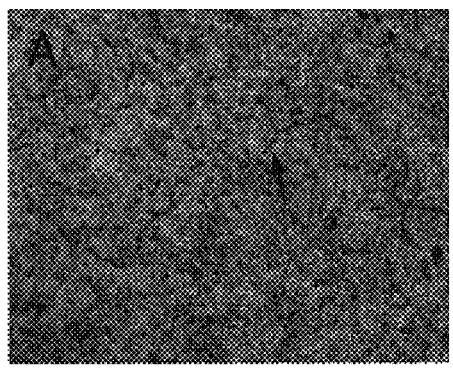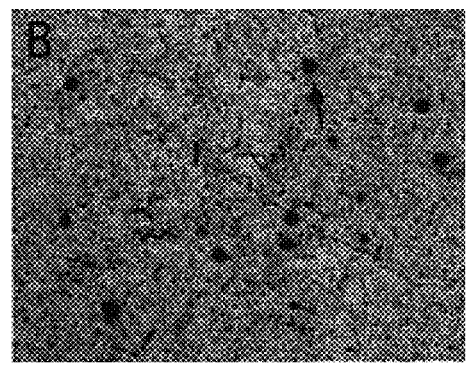
Fig. 16A  Fig. 16B
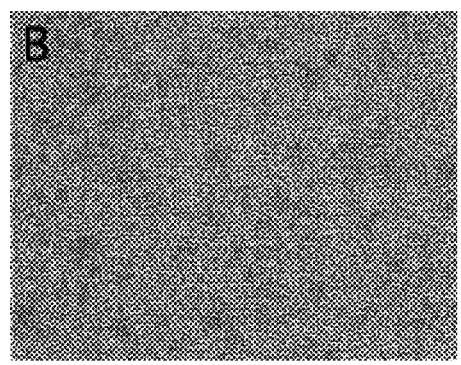
Fig. 17A  Fig. 17B

SEQUENCE LISTING

<160> NUMBER OF SEQ ID NOS: 11

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 25
<212> TYPE: PRT
<213> ORGANISM: Homo sapiens

<400> SEQUENCE: 2

Asp Gln Leu Gly Lys Asn Glu Glu Gly Ala Pro Gln Glu Gly Ile Leu
1               5                   10                  15

Glu Asp Met Pro Val Asp Pro Asp Asn
            20                  25

<210> SEQ ID NO 3
<211> LENGTH: 26
<212> TYPE: PRT
<213> ORGANISM: Homo sapiens

<400> SEQUENCE: 3

Lys Asp Gln Leu Gly Lys Asn Glu Glu Gly Ala Pro Gln Glu Gly Ile
1               5                   10                  15

Leu Glu Asp Met Pro Val Asp Pro Asp Asn
            20                  25

<210> SEQ ID NO 4
<211> LENGTH: 23
<212> TYPE: PRT
<213> ORGANISM: Homo sapiens

<400> SEQUENCE: 4

```
Lys Asp Gln Leu Gly Lys Asn Glu Glu Gly Ala Pro Gln Gly Ile
1               5                   10                  15

Leu Glu Asp Met Pro Val Asp
            20
```

<210> SEQ ID NO 5
<211> LENGTH: 8
<212> TYPE: PRT
<213> ORGANISM: Homo sapiens

<400> SEQUENCE: 5

```
Lys Asn Glu Glu Gly Ala Pro Gln
1               5
```

<210> SEQ ID NO 6
<211> LENGTH: 31
<212> TYPE: PRT
<213> ORGANISM: Homo sapiens

<400> SEQUENCE: 6

```
Glu Gly Ile Leu Glu Asp Met Pro Val Asp Pro Asp Asn Glu Ala Tyr
1               5                   10                  15

Glu Met Pro Ser Glu Glu Gly Tyr Gln Asp Tyr Glu Pro Glu Ala
            20                  25                  30
```

<210> SEQ ID NO 7
<211> LENGTH: 8
<212> TYPE: PRT
<213> ORGANISM: Mus musculus

<400> SEQUENCE: 7

```
Lys Gly Glu Glu Gly Val Pro Gln
1               5
```

<210> SEQ ID NO 8
<211> LENGTH: 31
<212> TYPE: PRT
<213> ORGANISM: Mus musculus

<400> SEQUENCE: 8

```
Glu Gly Ile Leu Glu Asp Met Pro Val Asp Pro Gly Ser Glu Ala Tyr
1               5                   10                  15

Glu Met Pro Ser Glu Glu Gly Tyr Gln Asp Tyr Glu Pro Glu Ala
            20                  25                  30
```

<210> SEQ ID NO 9
<211> LENGTH: 11
<212> TYPE: PRT
<213> ORGANISM: Artificial
<220> FEATURE:
<223> OTHER INFORMATION: Epitope bound by antibody as depicted in Figure
      8

<400> SEQUENCE: 9

```
Asp Met Pro Val Asp Pro Asp Asn Glu Ala Tyr
1               5                   10
```

<210> SEQ ID NO 10
<211> LENGTH: 8
<212> TYPE: PRT
<213> ORGANISM: Artificial
<220> FEATURE:
<223> OTHER INFORMATION: Immunogenic peptide

```
-continued

<400> SEQUENCE: 10

Cys Gly Gly Asp Met Pro Val Asp
1               5

<210> SEQ ID NO 11
<211> LENGTH: 8
<212> TYPE: PRT
<213> ORGANISM: Artificial
<220> FEATURE:
<223> OTHER INFORMATION: Immunogenic peptide

<400> SEQUENCE: 11

Cys Gly Gly Val Asp Pro Asp Asn
1               5
```

TRUNCATED FRAGMENTS OF ALPHA-SYNUCLEIN IN LEWY BODY DISEASE

CROSS-REFERENCE TO RELATED APPLICATIONS

The present application is a continuation-in-part of U.S. application Ser. No. 10/969,335, filed Oct. 19, 2004, which is a continuation-in-part of U.S. application Ser. No. 10/850,570 filed May 19, 2004, now abandoned, which claims the benefit under 35 USC §119(e) of U.S. application Ser. No. 60/471,929, filed May 19, 2003, each of which are incorporated by reference in its entirety for all purposes. This application, filed Jul. 29, 2005, is also continuation-in-part of PCT/US04/15836 filed May 19, 2004, published as WO 05/013889, which claims the benefit under 35 USC §119(e) of U.S. application Ser. No. 60/471,929, filed May 19, 2003, each incorporated by reference in its entirety for all purposes.

BACKGROUND

Lewy body diseases (LBDs) are characterized by degeneration of the dopaminergic system, motor alterations, cognitive impairment, and formation of Lewy bodies (LBs). (McKeith et at., *Clinical and pathological diagnosis of dementia with Lewy bodies (DLB): Report of the CDLB International Workshop, Neurology* (1996) 47:1113-24). LBDs include Parkinson's disease, Diffuse Lewy body disease (DLBD), Lewy body variant of Alzheimer's disease (LBV), and combined PD and Alzheimer's disease (AD) and the syndromes identified as multiple system atrophy (MSA). Dementia with Lewy bodies (DLB) is a term coined to reconcile differences in the terminology of LBDs. Disorders with LBs continue to be a common cause for movement disorders and cognitive deterioration in the aging population (Galasko et at., *Clinical-neuropathotogical correlations in Alzheimer's disease and related dementias. Arch. Neurol.* (1994) 51:888-9S). Although their incidence continues to increase creating a serious public health problem, to date these disorders lack approved treatments (Tanner et at., *Epidemiology of Parkinson's disease and akinetic syndromes, Curr. Opin. Neurol.* (2000) 13:427-30). The cause for LBD's is controversial and multiple factors have been proposed to play a role, including various neurotoxins and genetic susceptibility factors.

AD, PD, and DLBD are the most commonly found neurodegenerative disorders in the elderly. Recent epidemiological studies have demonstrated a close clinical relationship between AD and PD, as about 30% of Alzheimer's patients also have PD. Compared to the rest of the aging population, patients with AD are thus more likely to develop concomitant PD. Furthermore, PD patients that become demented usually have developed classical AD. Although each neurodegenerative disease appears to have a predilection for specific brain regions and cell populations, resulting in distinct pathological features, PD, AD, and DLBD also share common pathological hallmarks. Patients with familial AD, Down syndrome, or sporadic AD develop LBs on the amygdala, which are the classical neuropathological hallmarks of PD. Additionally, each disease is associated with the degeneration of neurons, interneuronal synaptic connections and eventually cell death, the depletion of neurotransmitters, and abnormal accumulation of misfolded proteins, the precursors of which participate in normal central nervous system function. Biochemical studies have confirmed a link between AD, PD and DLB.

In recent years, new hope for understanding the pathogenesis of LBD has emerged. Specifically, several studies have shown that the synaptic protein alpha-synuclein plays a central role in PD pathogenesis since: (1) this protein accumulates in LBs (Spillantini et al., *Nature* (1997) 388: 839-40; Takeda et al., *J. Pathol.* (1998) 152:367-72; Wakabayashi et al., *Neurosci. Lett.* (1997) 239:45-8), (2) mutations in the alpha-synuclein gene co-segregate with rare familial forms of parkinsonism (Kruger et al., *Nature Gen.* (1998) 18:106-8; Polymeropoulos, et al., *Science* (1997) 276:2045-7) and, (3) its overexpression in transgenic mice (Masliah et al., *Science* (2000) 287:1265-9) and *Drosophila* (Feany et al., *Nature* (2000) 404:394-8) mimics several pathological aspects of PD. Thus, the fact that accumulation of alpha-synuclein in the brain is associated with similar morphological and neurological alterations in species as diverse as humans, mice, and flies suggests that this molecule contributes to the development of PD.

The neuritic plaques that are the classic pathological hallmark of AD consist essentially of amyloid beta (Aβ) peptide, an amino acid proteolytic product of the amyloid precursor protein (APP), and NAC, a 35 amino acid proteolytic fragment of alpha-synuclein. Both Aβ and NAC were first identified in amyloid plaques as proteolytic fragments of their respective full-length proteins, for which the full-length cDNAs were identified and cloned. (Iwai A., *Biochim. Biophys. Acta* (2000) 1502:95-109); Masliah et al., *AM. J. Pathol* (1996) 148:201-10; Ueda et al., *Proc. Natl. Acad. Sci. USA* (1993) 90:11282-6).

Alpha-synuclein is part of a large family of proteins including beta- and gamma-synuclein and synoretin. Alpha-synuclein is expressed in the normal state associated with synapses and is believed to play a role in neural plasticity, learning and memory. Mutations in human (h) alpha-synuclein that enhance the aggregation of alpha-synuclein have been identified (Ala30Pro and Ala53Thr) and are associated with rare forms of autosomal dominant forms of PD. The mechanism by which these mutations increase the propensity of alpha-synuclein to aggregate are unknown.

SUMMARY OF THE CLAIMED INVENTION

The invention provides methods of screening for an agent having a pharmacological activity useful for treating a Lewy Body Disease (LBD). The method involves contacting the agent with a fragment of alpha-synuclein, wherein the fragment is characterized by presence of at least 100 contiguous amino acids of intact (i.e., full-length) alpha-synuclein and a deletion of 1-25 contiguous amino acids from the C-terminus of intact alpha-synuclein; and determining the rate or extent of aggregation of the fragment of alpha-synuclein, wherein a reduction in the rate or extent of aggregation relative to a control lacking the agent indicates the agent has the pharmacological activity.

Optionally, the fragment has a C-terminus at a residue within residues 115 and 125 of intact alpha-synuclein with residues numbered according to SEQ ID NO:1. Preferred fragments include alpha-synuclein SN1-115, SN1-116, SN1-117, SN1-118, SN1-119, SN 1-120, SN1-121, SN1-122, SN1-123, SN1-124, and SN1-125. SN1-115, SN1-122, SN1-133 and SN1-135 are particularly preferred. Optionally, the fragment of alpha-synuclein is 1-X, wherein X is 130-139. Optionally, the fragment of alpha-synuclein bears a mutation associated with a hereditary LBD, such as an A53T mutation. Optionally, the method involves an additional step of conducting a trial in a human having a LBD or an animal model of LBD to determine whether the agent treats or inhibits a symptom of the LBD.

The invention further provides methods of screening for an agent having a pharmacological activity useful for treating a Lewy Body Disease (LBD). The methods involve contacting the agent with phosphorylated alpha-synuclein or a phosphorylated fragment thereof, wherein the fragment is characterized by presence of at least 100 contiguous amino acids of intact alpha-synuclein and a deletion of 1-11 contiguous amino acids from the C-terminus of intact alpha-synuclein; and determining the rate or extent of aggregation of the alpha synuclein or fragment of alpha-synuclein, wherein a reduction in the rate or extent of aggregation relative to a control lacking the agent indicates the agent has the pharmacological activity. Optionally, the agent is contacted with intact alpha synuclein or SN1-133 or SN1-135 numbered according to SEQ ID NO:1. Optionally, intact alpha synuclein or the fragment of alpha-synuclein bears a mutation associated with a hereditary LBD. Optionally, the mutation is an A53T mutation. Optionally, the method further comprises conducting a trial in a human having a LBD or an animal model of LBD to determine whether the agent treats or inhibits a symptom of the LBD.

The invention further provides methods of screening an agent for a pharmacological activity useful in treating a LBD (e.g., Parkinson's disease or DLBD). These methods comprise contacting a cell expressing alpha-synuclein and processing the alpha-synuclein into a fragment with an agent. The fragment is characterized by presence of at least 100 contiguous amino acids of intact alpha-synuclein and a deletion of 1-25 contiguous amino acids from the C-terminus of intact alpha-synuclein. One then determines a level of the fragment in the cell relative to a baseline level in the same cell type in the absence of the agent, a reduction in the level of the fragment relative to the baseline indicating the agent has the pharmacological activity useful in treating a LBD. Optionally, the fragment of alpha-synuclein has a C-terminus at a residue between 115 and 125 of intact alpha-synuclein. Preferred fragments are SN1-115, SN1-116, SN1-117, SN1-118, SN1-119, SN1-1-120, SN1-121, SN1-122, SN1-123, SN1-124, and SN1-125 of alpha synuclein. SN1-115, SN1-119, SN1-122, SN1-133 and SN1-135 are particularly preferred. Optionally, the fragment of alpha-synuclein is 1-X, wherein X is 130-139. Optionally, the fragment of alpha-synuclein bears a mutation associated with a hereditary LBD, such as an A53T mutation. The cell can be a human cell, a neuronal cell, a dopaminergic cell or a nondopaminergic cell. Optionally, the cell is a PC12 or Sy5Y cell. Optionally, the method involves a step of conducting a trial in a human having a LBD or an animal model of LBD to determine whether the agent treats or inhibits a symptom of the LBD.

The invention further provides methods of screening for an agent having a pharmacological activity useful for treating a LBD (e.g., Parkinson's disease or DLBD). The methods involve contacting a transgenic animal expressing a fragment of alpha-synuclein, wherein the fragment is characterized by presence of at least 100 contiguous amino acids of intact alpha-synuclein and a deletion of 1-25 contiguous amino acids from the C-terminus of intact alpha-synuclein; and determining a level of aggregated forms of the fragment in the brain of the transgenic animal relative to a baseline level of aggregated forms of the fragment in a comparable transgenic animal in the absence of the agent, a reduction in the level of the aggregated forms fragment relative to the baseline indicating the agent has a pharmacological activity useful in treating a LBD. Optionally, the fragment of alpha-synuclein has a C-terminus at a residue between 115 and 125 of intact alpha-synuclein. Preferred fragments include SN1-115, SN1-116, SN1-117, SN1-118, SN1-119, SN1-120, SN1-121, SN1-122, SN1-123, SN1-124, and SN1-125 of alpha synuclein. SN1-115, SN1-119, SN1-122, SN133 and SN1135 are particularly preferred. Optionally, the fragment of alpha-synuclein is 1-X, wherein X is 119-139. Optionally, the fragment of alpha-synuclein bears a mutation associated with a hereditary LBD, such as an A53T mutation. Optionally, the transgenic animal is a rodent. The transgenic animal can also be a *Drosophila*. Optionally, the method involves conducting a trial in a human having a LBD or an animal model of LBD to determine whether the agent treats or inhibits a symptom of the LBD.

The invention further provides methods of screening an agent for a pharmacological activity useful for treating a LBD (e.g., Parkinson's disease or DLBD). The methods involve contacting a transgenic animal expressing alpha-synuclein and processing the alpha-synuclein into a fragment with an agent, wherein the fragment is characterized by presence of at least 100 contiguous amino acids of intact alpha-synuclein and a deletion of 1-25 contiguous amino acids from the C-terminus of intact alpha-synuclein; and determining a level of the fragment in a neuronal cell relative to a baseline level in the absence of the agent, a reduction in the level of the fragments relative to the baseline indicating the agent has the pharmacological activity useful for treating the LBD. Optionally, the fragment of alpha-synuclein has a C-terminus at a residue between 115 and 125 of intact alpha-synuclein. Preferred fragments include SN1-115, SN1-116, SN1-117, SN1-118, SN1-119, SN1-120, SN1-121, SN1-122, SN1-123, SN1-124, and SN1-125 of alpha synuclein. SN1-115, SN1-119, SN1-122, SN133 and SN135 are particularly preferred. Optionally, the fragment of alpha-synuclein is 1-X, wherein X is 130-139. Optionally, the fragment of alpha-synuclein bears a mutation associated with a hereditary LBD, such as an A53T mutation. Optionally, the transgenic animal is a rodent, mouse or *Drosophila*. Optionally, the method involves a step of conducting a trial in a human having a LBD or an animal model of LBD to determine whether the agent treats or inhibits a symptom of the LBD.

The invention further provides a transgenic animal having a genome comprising a transgene comprising a promoter operably linked to a nucleic acid segment encoding a fragment of alpha-synuclein wherein the fragment is characterized by presence of at least 100 contiguous amino acids of intact alpha-synuclein and a deletion of 1-25 contiguous amino acids from the C-terminus of intact alpha-synuclein; wherein expression of the fragment in the transgenic animal disposes the animal to develop at least one characteristic of a LBD. Optionally, the fragment of alpha-synuclein is selected from the group consisting of SN1-115, SN1-116, SN1-117, SN1-118, SN1-119, SN1-120, SN1-121, SN1-122, SN1-123, SN1-124, and SN1-125. SN1-115, SN1-119, SN1-122, SN133 and SN135 are particularly preferred. Optionally, the fragment of alpha-synuclein is 1-X, wherein X is 130-139. Optionally, the promoter is a PDGF promoter. Optionally, at least one characteristic is an impairment of motor function. Optionally, at least one characteristic of the transgenic animal is an impairment of cognitive function. Optionally, the transgenic animal is a rodent, mouse or *Drosophila*.

The invention further provides methods of detecting presence or susceptibility to an LBD in a patient. The methods involve detecting a level of a fragment of alpha-synuclein in cerebrospinal fluid, wherein the fragment is characterized by presence of at least 100 contiguous amino acids of intact alpha-synuclein and a deletion of 1-25 contiguous amino acids from the C-terminus of intact alpha-synuclein. A change in level, usually an increase, relative to the baseline level in undiseased individuals indicating presence or susceptibility to LBD.

The invention further provides an antibody that specifically binds to a fragment of alpha-synuclein, wherein the fragment is characterized by presence of at least 100 contiguous amino acids of intact alpha-synuclein and a deletion of 1-25 contiguous amino acids from the C-terminus of intact alpha-synuclein; without specifically binding to full-length alpha synuclein. Preferred fragments include SN1-115, SN1-116, SN1-117, SN1-118, SN1-119, SN1-120, SN1-121, SN1-122, SN1-123, SN1-124, and SN1-125 of alpha synuclein. SN1-115, SN1-19, SN1-122, SN133 and SN135 are particularly preferred. Optionally, the fragment is 1-X, wherein X is 130-139. Optionally, the antibody is a human, humanized, chimeric antibody. Optionally, the antibody is monoclonal. Optionally, the antibody has human isotype IgG1.

The invention further provides methods of diagnosing presence or susceptibility to LBD. The methods involve administering to a patient an antibody that specifically binds to a fragment of alpha-synuclein having a free C-terminus at residues 115-135 without specifically binding to full length synuclein; and determining a level of binding of the antibody in the patients, wherein a higher level of binding relative to a base line level in undiseased individuals indicates presence or susceptibility to the LBD. Preferably the antibody specifically binds to the free C-terminus of a fragment selected from the group consisting of SN1-115, SN1-119, SN1-122, SN133 and SN135.

The invention further provides methods of effecting treatment or prophylaxis of a LBD, comprising administering to a patient suffering from or at risk of a LBD, an effective regime of a fragment of alpha-synuclein, wherein the fragment is characterized by presence of at least 100 contiguous amino acids of intact alpha-synuclein and a deletion of 1-25 contiguous amino acids from the C-terminus of intact alpha-synuclein, and thereby effecting treatment or prophylaxis of the LBD. Optionally, the fragment of alpha-synuclein is SN1-115, SN1-116, SN1-117, SN1-118, SN1-119, SN1-120, SN1-121, SN1-122, SN1-123, SN1-124, and SN1-125 of alpha synuclein. SN1-115, SN1-119, SN1-122, SN133 and SN135 are particularly preferred. Optionally, the fragment is 1-X, wherein X is 130-139. Optionally, the method further comprises administering an adjuvant that augments an immune response comprising antibodies to the fragment. Optionally, the fragment is linked to a carrier forming a fusion protein, wherein the carrier augments an immune response comprising antibodies to the fragment.

The invention further provides methods of effecting treatment or prophylaxis of a LBD. The method involves administering to a patient suffering from or at risk of a LBD an effective regime of an antibody that specifically binds to a fragment of alpha-synuclein, wherein the fragment is selected from the group consisting of SN1-115, SN1-116, SN1-117, SN1-118, SN1-119, SN1-120, SN1-121, SN1-122, SN1-123, SN1-124, and SN1-125 and 1-X, wherein X is 130-139, without binding to intact alpha-synuclein, whereby the antibody effects prophylaxis or treatment of the disease. SN1-115, SN1-119, SN1-122, SN133 and SN135 are particularly preferred.

The invention further provides methods of effecting treatment or prophylaxis of a LBD. The methods comprise administering to a patient suffering from or at risk of a LBD, an effective regime of phosphorylated alpha synuclein or a phosphorylated fragment of alpha-synuclein, wherein the fragment is characterized by presence of at least 100 contiguous amino acids of intact alpha-synuclein and a deletion of 1-10 contiguous amino acids from the C-terminus of intact alpha-synuclein; and thereby effecting treatment or prophylaxis of the LBD. Optionally, the fragment is SN1-133 or SN1-135. Optionally, the method further comprises administering an adjuvant that augments an immune response comprising antibodies to the fragment. Optionally, the fragment is linked to a carrier forming a fusion protein, wherein the carrier augments an immune response comprising antibodies to the fragment.

The invention further provides a method of isolating a protease that cleaves intact alpha-synuclein to form a fragment, wherein the fragment is characterized by presence of at least 100 contiguous amino acids of intact alpha-synuclein and a deletion of 1-25 contiguous amino acids from the C-terminus of intact alpha-synuclein. SN1-115, SN1-119, SN1-122, SN133 and SN135 are particularly preferred. The method involves identifying an inhibitor of the protease; contacting the inhibitor with a cellular or tissue extract containing the protease, whereby the protease binds to the inhibitor; and releasing the protease from the inhibitor. Optionally, the inhibitor is a peptide of alpha-synuclein comprising a contiguous segment of at least 5 residues and up to 20 residues of intact alpha-synuclein between positions 111 and 130. Alternatively the peptide is an inhibitor comprising least 5 residues of intact alpha-synuclein between positions 129 and 139. Optionally, the peptide comprises a contiguous segment of at least 5 residues between positions 118 and 122. Optionally, the peptide comprises a contiguous segment of at least four residues between positions 114 and 117. Optionally, at least one of the residues is a transition state analog.

The invention further provides a monoclonal antibody that specifically binds to an epitope within residues 109-120 of alpha synuclein. Optionally, the monoclonal antibody is chimeric, humanized or human.

The invention further provides a monoclonal antibody that specifically binds to an epitope within residues 115-123 of alpha synuclein.

The invention further provides a monoclonal antibody that specifically binds to a discontinuous epitope within residues 43-51 and 58-65 of alpha synuclein. Optionally, the antibody is chimeric, humanized or human.

The invention further provides an end-specific monoclonal antibody that specifically binds to isolated full-length alpha-synuclein having a free C-terminus without specifically binding to a fusion protein comprising alpha synuclein having a C-terminus linked to a second polypeptide. Optionally, the antibody is chimeric, humanized or human.

The invention further provides methods of detecting presence or susceptibility to a Lewy body disease in a patient. The methods involves determining a level of alpha-synuclein phosphorylated at position 129 or phosphorylated or nitrated at position 125 of alpha-synuclein in a sample from a brain of the patient, an elevated level relative to the mean level in a population of undiseased individuals indicating the patient has or is susceptible to a Lewy body disease. The invention provides other methods of detecting presence or susceptibility to a Lewy body disease in a patient by determining a level of ubiquitinated alpha synuclein in a sample from a brain of the patient, an elevated level relative

BRIEF DESCRIPTION OF THE FIGURES

FIGS. 14A, B, C, E, and F show different preparations from different patients

FIGS. 16A and B respectively show labeling of Lewy bodies and neuritis with the SN1-119 end-specific polyclonal antibody ELADW-101.

FIGS. 17A and B are controls from a normal individual stained with ELADW-101.

DEFINITIONS

Figures 1A, 1B:
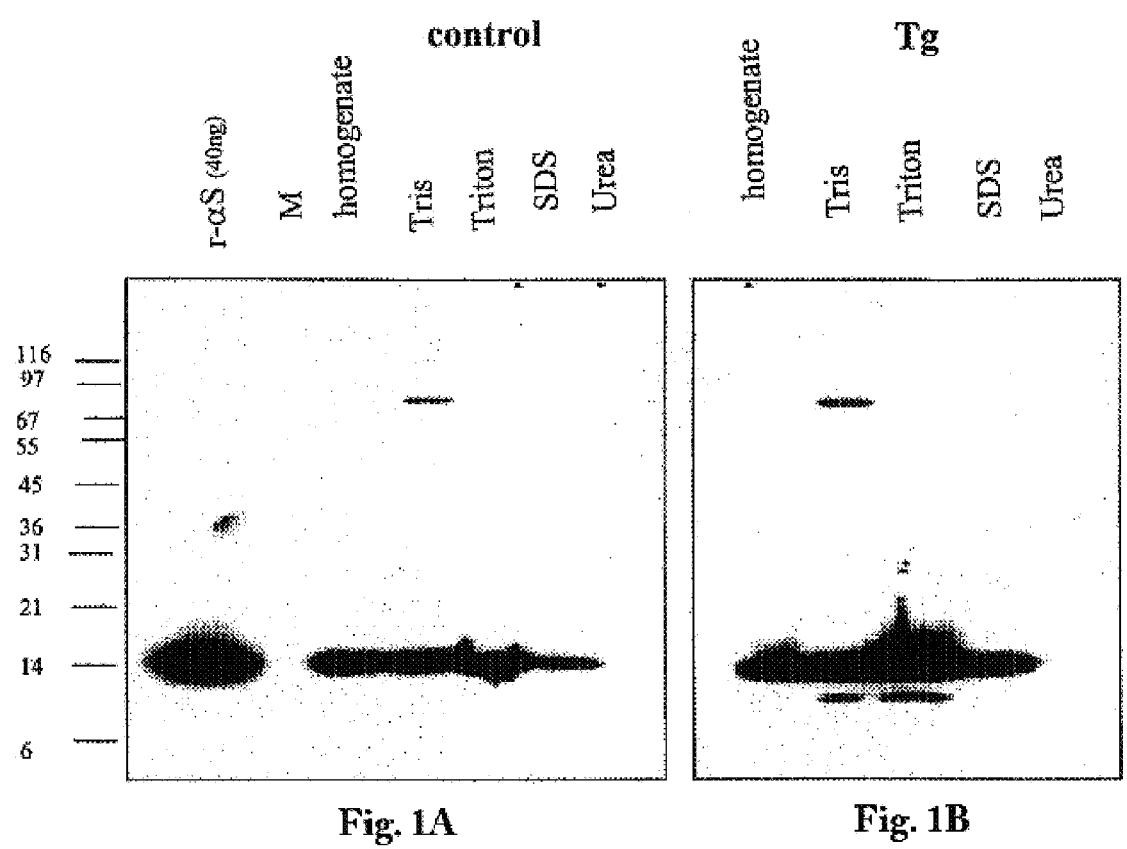
FIGS. 1A and B show a Western blot of various extracts from the cortex and hippocampus of a transgenic mouse (B) and a matched control (A) with a polyclonal antibody that binds to an epitope within SN115-122.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

A "pharmacological" activity means that an agent exhibits an activity in a screening system that indicates that the agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

In the context of molecular weight determinations based on gel electrophoresis, the term "about" indicates the standard deviation of molecular weight expected due to experimental error in repetitions of the method under the same conditions. The molecular weight determination of 12 kDa for certain fragments of alpha-synuclein applies to determinations using a tricine buffer.

The phrases "specifically binds" refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule such as antibody that specifically binds to a protein often has an association constant of at least $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

For purposes of classifying amino acids substitutions as conservative or non-conservative, amino acids are grouped as follows: Group I (hydrophobic side chains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab° F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "patient" includes human and other mammalian subjects that receive either prophylactic or therapeutic treatment.

Competition between antibodies is determined by an assay in which the immunoglobulin under test inhibits specific binding of a reference antibody to a common antigen, such as alpha-synuclein. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, Antibodies, A Laboratory Manual, Cold Spring Harbor Press (1988)); solid phase direct label RIA using I-125 label (see Morel et al., Molec. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

Epitope co-ordinates are approximate (±2 amino acids). Not every amino acid within an epitope is necessarily required for binding.

Compositions or methods "comprising" one or more recited elements may include other elements not specifically recited. For example, a composition that comprises alpha-synuclein peptide encompasses both an isolated alpha-synuclein peptide and alpha-synuclein peptide as a component of a larger polypeptide sequence.

Unless otherwise apparent from the context, each embodiment, element, step or feature of the invention can be used in combination with any other.

DETAILED DESCRIPTION OF THE INVENTION

I. General

The invention is premised in part on the identification of novel fragments of alpha-synuclein in patients with Lewy Body Disease (LBD) and transgenic animal models thereof. These diseases are characterized by aggregations of alpha-synuclein. The fragments have a truncated C-terminus relative to full-length alpha-synuclein. Some fragments are characterized by a molecular weight of about 12 kDa (corresponding to SN1-119), 12.5 kDa (corresponding to SN1-122), 13.5 kDa (which fragment is found only in patients with LBD) and 15 kDa (probably corresponding to SN1-133 or SN1-135) as determined by SDS gel electrophoresis in tricine buffer and a truncation of at least ten contiguous amino acids from the C-terminus of natural synuclein prone to aggregation and changes its intracellular path from proteosomes to lysosomes. Thus, ubiquitination can both increase degradation of alpha synuclein and promote its aggregation. Modulation of ubiquitination can therefore be useful in treating synucleinopathic disease.

The invention provides several methods for screening agents for activity useful in treating LBDs. Some methods identify agents that inhibit the cleavage reaction that generates the novel fragments of the invention. Other method identify agents that inhibit aggregation of the products of the cleavage reaction. Such inhibitors are useful for treatment of LBD's. Inhibitors of the cleavage reaction are also useful for affinity purification of the protease responsible for the cleavage reaction.

The invention also provides transgenic animal models and cells expressing fragments of alpha-synuclein as described above. The transgenic animal models and cells are disposed to develop characteristics of Lewy body disease, including Lewy bodies containing aggregations of the fragments. The animal models and cells can be used in the screening methods described above.

The invention further provides end-specific antibodies that specifically bind to fragments of alpha-synuclein without specifically binding to intact alpha-synuclein per se. These antibodies are useful for in vivo imaging of alpha-synuclein aggregations and also in methods of treatment. The novel alpha-synuclein fragments can also be used in methods of treatment, optionally, in combination with an adjuvant.

II. Alpha-Synuclein Fragments

Human alpha-synuclein is a peptide of 140 amino acids having the following amino acid sequence:

```
                                                    (SEQ ID NO:1)
MDVFMKGLSK AKEGVVAAAE KTKQGVAEAA GKTKEGVLYV GSKTKEGVVH

GVATVAEKTK EQVTNVGGAV VTGVTAVAQK TVEGAGSIAA ATGFVKKDQL

GKNEEGAPQE GILEDMPVDP DNEAYEMPSE EGYQDYEPEA
``` alpha-synuclein. The site of cleavage preferably occurs after residue 115 and before residue 136 of natural human alpha-synuclein. Particularly preferred sites of cleavage are between residues 115 and 116, 119 and 120, between residues 122 and 123, between residues 132 and 133 and between residues 135 and 136. The identification of these novel fragments of alpha-synuclein has a number of application in for example, drug discovery, diagnostics, therapeutics, and transgenic animals.

The invention is further premised in part on the result that phosphorylation synuclein partitions more to the particulate (Lewy body enriched fraction) relative to the soluble cytosolic fraction in patients with synucleinopathic disease relative to controls. Phosphorylation occurs at position 129 of alpha synuclein. Although an understanding of mechanism is not required for practice of the invention, it is proposed that phosphorylation of alpha synuclein drives subsequent processing to truncated forms (i.e., cleavages between residues between residues 132 and 133 and between residues 135 and 136) and aggregation of alpha synuclein. The invention further shows that small amounts of alpha synuclein in insoluble fractions from patients with synucleinopathic disease are ubiquitinated at lysine residues 6, 10, 12, 21, 23, 32 and 34. Ubiquitination is known to have a role in degradation of proteins (see, e.g., Cierchanover, EMBO J. 17, 7151-7160 (1998)). Ubiquitination also renders alpha (Ueda et al., Proc. Natl. Acad. Sci. USA (1993) 90:11282-6); GenBank accession number: P37840). The protein has three recognized domains, a KTKE repeat domain covering amino acids 1-61, a NAC (Non-amyloid component) domain running from about amino acids 60-95, and a C-terminal acidic domain running from about amino acid 98 to 140.

Some novel fragments of the invention have C-terminal truncations of at least ten contiguous amino acids, preferably at least 15 contiguous amino acids, and optionally at up to 20, 22, 23 or 25 amino acids. The fragments include all or substantially all (i.e., at least 100 contiguous residues from alpha-synuclein other than the deletion). Some fragments also have relatively short truncations at the N-terminus of up to 20 amino acids, such as deletions of residues 1-4, 1-6, 1-10 and 1-12. Some fragments have N-terminal deletions of residues 1-23, 1-38 or 1-45. Preferred fragments are SN1-115, SN1-116, 1-117, SN1-118, SN1-119, SN1-120, SN1-121, SN1-122, SN1-123, SN1-124, SN1-125, SN1-126, SN1-127, SN1-128, SN1-129 and SN1-130. Particularly preferred fragments are SN1-115, SN1-119, SN1-120, SN1-121, SN1-122, SN1-123; SN1-124 and SN1-125. Especially preferred fragments are SN1-115, SN1-119, SN1-122 SN1-133 and SN1-135. The cleavage reaction preferably occurs at a peptide bond between amino acid residues 115 and 116, or 118 and 136, e.g., particularly between residue 119 and 120 or residues 122 and 123 or residues 133-134 or residues 135-136.

The C-terminal fragments resulting from cleavage are also included in the invention and can be used in the methods described below. These fragments include SN116-140, SN117-140, SN118-140, SN119-140, SN119-140, SN120-140, SN121-140, SN122-140, SN123-140, SN124-140, SN125-140, SN126-140, SN1-127-140, SN128-140, SN129-140, SN 130-140 and SN131-140. Preferred fragments are SN116-140, SN120-140, SN123-140, SN 134-140 and SN136-140.

Other fragments of the invention include N-terminal fragments of alpha-synuclein of about 6 to 7 kDa (as determined by SDS electrophoresis) or 50-80 amino acids. Other fragments of the invention include N-terminal fragments of alpha-synuclein that are free of 1-10 amino acids from the C-terminus of intact alpha-synuclein, i.e., SN 1-X, wherein X is 130-139. Some fragments are characterized by specific binding to antibodies ELADW43 (free N-terminus) and 5C12 (111-118) and lack of specific binding to 8A5 (free C-terminus), LB509 (115-123) and ELADW47 (115-122). Some fragments are characterized by specific binding to ELADW43 (intact N-terminus) and 5C12 (111-118), LB509 (115-123) and ELADW47 (115-122) and lack of specific binding to 8A5 (free C-terminus). Some fragments are characterized by specific binding to ELADW43 (free N-terminus) and 5C12 (111-118), LB509 (115-122) and ELADW47 (118-123) and 8A5 (free C-terminus) and lack of specific binding to ELADW43 (free N-terminus).

Some fragments or full-length alpha synuclein are phosphorylated at position 125 or 129 or nitrated at the tyrosine residue occupying position 125 of alpha synuclein. Fragments retaining amino acid serine 125 or full-length alpha synuclein can also be phosphorylated at this position. Detection of enhanced phosphorylation or nitration at position 125 or phosphorylation at position 129 in a patient relative to the mean in a population of undiseased individuals is an indication of a Lewy body disease. Detection can be performed using an antibody specific for alpha-synuclein phosphorylated or nitrated at position 125. A level is considered enhanced if greater than the mean plus one standard deviation in a population of undiseased individuals.

The invention also provides isolated peptides of up to five or ten contiguous residues of alpha synuclein containing at least one of the above-mentioned ubiquitination sites. These peptides can be used to compete with sites in the full-length alpha-synuclein for ubiquitination or as immunogens to generate antibodies that block ubiquitination of full-length alpha-synuclein.

The fragments of the invention are distinct from the non-Aβ component of Alzheimer's disease amyloid (NAC) previously reported. This fragment consisting of at least 28 amino acids residues (residues 60-87) and optionally 35 amino acid residues (residues 61-95). See Iwai, et al., *Biochemistry*, 34:10139-10145); Jensen et al., *Biochem. J.* 310 (Pt 1): 91-94 (1995); GenBank accession number S56746.

Unless otherwise apparent from the context, reference to alpha-synuclein or its fragments includes the natural human amino acid sequence indicated above, or fragments thereof, as well as analogs including allelic, species and induced variants (e.g., E83Q, A90V, A76T). Amino acids of analogs are assigned the same numbers as corresponding amino acids in the natural human sequence when the analog and human sequence are maximally aligned. Analogs typically differ from naturally occurring peptides at one, two or a few positions, often by virtue of conservative substitutions. Some natural allelic variants are genetically associated with hereditary LBD. The term "allelic variant" is used to refer to variations between genes of different individuals in the same species and corresponding variations in proteins encoded by the genes. Allelic variants include E46K, A30P and A53T (the first letter indicates the amino acid in SEQ ID NO:1, the number is the codon position in SEQ ID NO:1, and the second letter is the amino acid in the allelic variant). Analogs can include any combination of allelic variants. The A53T variation is associated with enhanced levels of phosphorylation at position 129 of alpha synuclein in an individual having the mutation relative to the norm of phosphorylation in undiseased individuals who lack the mutation. Analogs exhibit at least 80 or 90% sequence identity with natural peptides. Some analogs also include unnatural amino acids or modifications of N or C terminal amino acids at one, two or a few positions. For example, the natural glutamic acid residue can be replaced with iso-aspartic acid. Examples of unnatural amino acids are D, alpha, alpha-disubstituted amino acids, N-alkyl amino acids, lactic acid, 4-hydroxyproline, gamma-carboxyglutamate, epsilon-N,N,N-trimethyllysine, epsilon-N-acetyllysine, O-phosphoserine, N-acetyl serine, N-formylmethionine, 3-methylhistidine, 5-hydroxylysine, omega-N-methylarginine, β-alanine, ornithine, norleucine, norvaline, hydroxyproline, thyroxine, gamma-amino butyric acid, homoserine, citrulline, and isoaspartic acid. Analogs typically specifically bind to a polyclonal antibody population generated against natural human alpha-synuclein, and each end of an analog of a specific fragment of a natural human alpha synuclein also specifically bind to a monoclonal antibody that is end specific for the respective end of the natural fragment. The invention also provides D-peptides, in which D-amino acids can be substituted for corresponding natural L-amino acids of alpha-synuclein at most or all positions. A fragment designated in the form SNx-y means a fragment of alpha synuclein that begins at amino acid X and ends at amino acid Y, and contains each amino acid between X and Y. Such a fragment can (but need not) be linked to a heterologous polypeptide but not to other amino acids of human alpha synuclein such that the fragment begins before X or ends after Y. Residues in a fragment are numbered according to SEQ ID NO:1 when the fragment is maximally aligned with SEQ ID NO:1 as described above using default parameters.

Alpha-synuclein, its fragments, and analogs can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., *Molecular Cloning: A Laboratory Manual* (C.S.H.P. Press, NY 2d ed., 1989).

III. Lewy Body Diseases

Lewy Body Disease (LBD) is characterized by degeneration of the dopaminergic system, motor alterations, cognitive impairment, and formation of Lewy bodies (LBs). (McKeith et al., *Clinical and pathological diagnosis of dementia with Lewy bodies (DLB): Report of the CDLB International Workshop, Neurology* (1996) 47:1113-24). Lewy Bodies are spherical protein deposits found in nerve cells. Their presence in the brain disrupts the brain's normal function interrupting the action of chemical messengers including acetylcholine and dopamine. Lewy Body diseases include Parkinson's disease (including idiopathic Parkinson's disease (PD)), Diffuse Lewy Body Disease (DLBD) also known as Dementia with Lewy Bodies (DLB), Combined Alzheimer's and Parkinson disease and multiple system atrophy (MSA). DLBD shares symptoms of both Alzheimer's and Parkinson's disease. DLBD differs from Parkinson's disease mainly in the location of Lewy Bodies. In DLBD Lewy Bodies form mainly in the cortex. In Parkinson's disease, they form mainly in the substantia nigra. Other Lewy Body diseases include Pure Autonomic Failure, Lewy body dysphagia, Incidental LBD, Inherited LBD (e.g., mutations of the alpha-synuclein gene, PARK3 and PARK4) and Multiple System Atrophy (e.g., Olivopontocerebellar Atrophy, Striatonigral Degeneration and Shy-Drager Syndrome).

IV. Transgenic Animals and Cells

The invention provides transgenic animals having a genome comprising a transgene comprising a nucleic acid segment encoding a C-terminal truncated form of alpha-synuclein as described above. Preferred truncated forms are SN1-115, SN1-119, SN1-122, SN1-133 and SN1-135. The transgene is preferably present in all or substantially of the somatic and germline cells of the transgenic animal. The nucleic acid segment encoding the C-terminal truncated form of alpha-synuclein is operably linked to one or more regulatory segments that allow the truncated form of alpha-synuclein to be expressed in neuronal cells of the animal. Promoters such as the rat neuron specific enolase promoter, human beta-actin gene promoter, human platelet derived growth factor B (PDGF-B) chain gene promoter, rat sodium channel gene promoter, mouse myelin basic protein gene promoter, human copper-zinc superoxide dismutase gene promoter, and mammalian POU-domain regulatory gene promoter can be used. The PDGF promoter is particularly suitable. Optionally, an inducible promoter is used. The mouse metallothionine promoter, which can be regulated by addition of heavy metals such as zinc to the mouse's water or diet, is suitable. Such transgenic animals can be produced by the same general approaches described by (Masliah et al., Am. J. Pathol. (1996) 148:201-10 and Feany et al., Nature (2000) 404:394-8)) for transgenic animals with full-length alpha-synuclein or U.S. Pat. No. 5,811,633 (for transgenic animals with a mutant form of APP). Optionally, transgenic animals bearing a transgene expressing a truncated alpha-synuclein protein can be crossed with other transgenic models of neurogenic disease, such as models of Alzheimer's disease. For example, transgenic animals bearing a transgene expressing a truncated alpha-synuclein protein can be crossed with transgenic animals bearing a transgene expressed APP with a FAD mutation as described by e.g., Games et al., Nature 373, 523 (1995) McConlogue et al., U.S. Pat. No. 5,612,486, Hsiao et al., Science 274, 99 (1996); Staufenbiel et al., Proc. Natl. Acad. Sci. USA 94, 13287-13292 (1997); Sturchler-Pierrat et al., Proc. Natl. Acad. Sci. USA 94, 13287-13292 (1997); Borchelt et al., Neuron 19, 939-945 (1997)). The procedure for performing such a cross is described by e.g., Masliah et al., PNAS USA 98:12245-12250 (2001), which reports a cross between transgenic mice expressing a full length alpha-synuclein with PDAPP mice as described by Games et al Transgenic animals of the invention are preferably rodents, such as mice or rats, or insects, such as Drosophila. Transgenic animals can be produced by introduction of a transgene at the germline stage in which case all or substantially all (except for rare loss through somatic mutation) of the cells of the transgenic animal include the transgene integrated into the genome. Transgenes can be introduced by microinjection, nuclear transfer or viral infection into cells or animals. Lentiviruses are particularly suitable for the latter. Alternatively, transgenes can be introduced by viral infection into the brain of the animal. Such transgenes are not part of the germline of recipient animals but can be targeted to regions of the brain responsible for disease (e.g., the substantia nigra). Such animal models incorporate an alpha synuclein into the genome of brain cells and are disposed to develop at least one characteristic of synucleinopathic disease. Lentiviruses provide a suitable vehicle for so introducing an alpha synuclein transgene into the brain (see Brain Pathology 13, 364-372 (2003); Bjorklund, Trends Neurosci. 26, 386-92 (2003), Lotharius et al., J. Biol. Chem. 277, 38884-94 (2002), Zhou et al., Brain Research 866, 33-43 (2000)).

The expression of truncated forms of alpha-synuclein in animal models gives rise to animals disposed to develop at least one characteristic of a Lewy Body disease. Such characteristics include increased levels of intracellular deposits of alpha-synuclein, increased formation of Lewy bodies, and impaired cognitive and motor functions relative to normal nontransgenic animals of the same species. Such transgenic animals are useful for screening agents for pharmacological activity in treating Lewy Body disease.

The invention also provides cells transformed with truncated alpha-synuclein which form inclusion bodies containing aggregated truncated alpha-synuclein. The transformed cells are preferably neuronal cells, such as GT1-7 neuronal cells (Hsue et al. Am. J. Pathol. 157:401-410 (2000)), PC12 cells or SY5Y neuroblastoma cells. PEAK cells can also be used. The cells are preferably human cells. A vector comprising a segment encoding a truncated form of alpha-synuclein operably linked to one or more regulatory sequences that ensure expression of the truncated expression is transfected into the cells. Transfected cells can be used to screen agents for activity in clearing alpha-synuclein inclusions.

V. Screening Methods

The invention provide several screening methods to identify agents having a pharmacological activity useful in treating a LBD. The methods include screens that can be performed in vitro, in cells or transgenic animals, and which test a variety of parameters as an indication of activity. Agents determined to have an activity in these screens can be retested in secondary screens of animal models of LBD or in clinical trials to determine activity against behavioral or other symptoms of these diseases.

1. In Vitro

In vitro assays are performed to test the capacity of an agent to inhibit aggregation of truncated forms of alpha-synuclein, particularly SN1-115, SN1-119, SN1-122, SN1-133 and SN1-135. The basis format for analyzing in vitro aggregation of alpha-synuclein, albeit in the context of full-length alpha-synuclein, is described by (Wood, J. Biol. Chem. 274, 19509-19512 (1999)). Truncated fragments can be phosphorylated for performing the assay. The assay can also be performed with full-length phosphorylated alpha synuclein. Phosphorylation is preferably at position 129. Synuclein can be phosphorylated in vitro using a serine kinase. In the present methods, the assay is performed in the presence of an agent being tested. The rate or extent of aggregation of alpha-synuclein in the presence of an agent is determined and compared with the rate or extent of aggregation of alpha-synuclein in a contemporaneous or historical control in which the agent was omitted. A reduction in the rate or extent of aggregation in the presence of the agent relative to the control indicates that the agent has activity in inhibiting aggregation of truncated forms of alpha-synuclein. This activity is potentially useful in treating or preventing Lewy Body diseases.

2. Cellular Assays

Some cellular assays are performed on cells transfected with nucleic acids encoding truncated forms of alpha-synuclein as described above (particularly SN1-115, SN1-119, SN1-122, SN1-133 and SN1-135), optionally with a hereditary variation, such as Ala30Pro or Ala53Thr. Cells can also bear mutations in other genes associated with Parkinson's disease, such as leucine rich repeat kinase PARK8. Such cells are contacted with an agent under test, and the rate of extent of aggregation of the truncated alpha-synuclein is measured. The rate of extent of aggregation of alpha-synuclein is then compared to that of similarly transfected control cells in the absence of the agent. Aggregation can be monitored by immunohistochemical analysis, light microscopy, sedimentation, or by gel analysis. Gel analysis can detect formation of dimmers, trimers or higher oligomers as well as inability of synuclein to enter gels due to a high level of oligomerization. A reduction in the rate or extent of aggregation in the presence of the test agent relative to the control indicates the agent has activity has a pharmacological activity in inhibiting aggregation of truncated forms of alpha-synuclein. This activity is potentially useful in treating or preventing Lewy Body diseases.

Other cellular assays are performed on cells transfected with nucleic acids encoding full-length alpha-synuclein, optionally with a hereditary variation, such as Ala30Pro or Ala53Thr. Cells can also have mutations in other genes associated with Parkinson's disease such as leucine rich repeat kinase, PARK8. Similar assays can also be performed on cells naturally expressing alpha synuclein. Such cells are contacted with an agent under test and the rate or extent of formation of truncated forms of alpha-synuclein (particularly SN1-115, SN1-119, SN1-122, SN1-133 and SN 1-135) and/or phosphorylated or nitrated forms of synuclein is/are measured. The presence of these forms can be detected by Western blotting using one or more antibodies to alpha-synuclein. End specific antibodies (i.e., antibodies that bind to a truncated form without binding to full length alpha-synuclein) are particularly useful for this analysis. Collections of antibodies having different epitope specificities can also be used. For example, presence of truncated forms of alpha-synuclein can be shown by presence of bands when blotted with antibodies recognizing an epitope N-terminal of an amino acid segment defined approximately by amino acids 115-125 or 118-135 (particularly SN1-115, SN1-119, SN1-122, SN1-133, and SN1-135) of intact alpha-synuclein, and, and lack of bands when blotted with an antibody recognizing an epitope C-terminal of this region. The rate or extent of formation of truncated forms of alpha-synuclein and/or phosphorylated or nitrated forms in the presence of agent is compared with that of comparable control cells in the absence of agent. A reduction in the rate or extent of formation of truncated forms of alpha-synuclein in the presence of the test agent relative to the control indicates that the agent has a pharmacological activity that inhibits processing of alpha-synuclein to its truncated forms. This activity is useful for treating or preventing LBD.

3. Transgenic Animal Assays

Transgenic animals have a transgene expressing a truncated form of alpha-synuclein as described above (particularly SN1-115, SN1-119, SN1-122, SN1-133 or SN1-135), optionally with a hereditary variation, such as Ala30Pro or Ala53Thr. Transgenic animals can also bear mutations in other genes associated with Parkinson's disease such as leucine-rich repeat kinase, PARK8. Such an animal is contacted with an agent under test, and the rate of extent of aggregation of the truncated form of alpha-synuclein is measured compared with that in a contemporaneous or historical control. The control is usually a similar transgenic animal of the same species that has not been exposed to the agent. Aggregation of alpha-synuclein in a transgenic animal can be monitored by Western blotting or immunohistochemistry as described in the examples. Alternatively or additionally, activity of the agent in such transgenic animals can be determined from behavioral characteristics such as motor or cognitive characteristics, as described in the Examples. In such assays, pharmacological activity of the agent is shown by improved motor or cognitive characteristics (i.e., decrease impairment of such characteristics) relative to a comparable control transgenic animal not exposed to the agent.

Other assays are performed on transgenic animals having a transgene expressing a full-length form of alpha-synuclein, optionally with a hereditary variation, such as Ala30Pro or Ala53, or mutations in other genes associated with Parkinson's disease such as leucine rich repeat kinase, PARK8. Similar assays can be performed on nontransgenic animals expressing endogenous alpha synuclein. Such animals are contacted with an agent under test, and the rate or extent of appearance of truncated forms of alpha-synuclein (particularly SN1-115, SN1-119, SN1-122, SN1-133 or SN1-135) is detected, optionally with a hereditary variation, such as Ala30Pro or Ala53Th. Such forms can be detected using Western blotting or immunohistochemical analysis using appropriate anti-alpha-synuclein antibodies (as described for the cellular assays). The rate of extent of appearance of truncated forms of alpha-synuclein and/or phosphorylated or nitrated forms is compared with the rate or extent of appearance of such forms in a contemporaneous or historical control constituting a comparable transgenic animal that has not been exposed to the agent. A reduction in the rate or extent of appearance of the truncated forms of alpha-synuclein in the animal exposed to the test agent relative to the control indicates that agent has activity in inhibiting processing of full-length alpha-synuclein to truncated forms.

4. Agents to be Screened

Agents to be screened include antibodies to alpha-synuclein, peptides of alpha-synuclein, drugs known or suspected to have activity in treating a LBD, natural products, and combinatorial libraries. Preferred peptides of alpha-synuclein are relatively short peptides of 30, 25, 20 10, 5 or fewer amino acid including amino acids 114-1-17, 117-126, 11-8-125, 117-120, 120-124, 130-136, 132-138, 131-135, 132-134, 133-137, 134-136 of alpha-synuclein. Optionally, an amino acid immediately on the N-terminal side of the cleavage site that generates C-terminal truncated forms of alpha-synuclein is replaced with a transition state analog amino acid that forms a nonhydrolizable bond between the two amino acids flanking the cleavage site, e.g., between residues 115-116, 119-120, 122-123, 133-134 and 135-136 of alpha synuclein. Examples of analogs are transition state analogs are statine, hydroxyethelene, hydroxyethelamine, AHPPA, ACHPA, and derivatives thereof. One or more amino acids of a natural alpha-synuclein sequence can also be substituted with other natural amino acids.

Natural products to be screened can also be obtained from the National Cancer Institute's Natural Product Repository, Bethesda, Md. Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated herein by reference for all purposes). Peptide libraries can also be generated by phage display methods. See, e.g., Devlin, WO 91/18980. Combinatorial libraries and other compounds can initially be screened for suitability by determining their capacity to bind to alpha-synuclein.

VI. Toxicity Assays

Analogous strategies to those described in the screening assays can be used to determine whether existing drugs, foods, environmental toxins, and other compounds exert toxic effects via promotion of alpha-synuclein processing, phosphorylation or aggregation. Such assays are performed in the same manner as the screening assays. Toxic activity is indicated by the opposite result to pharmacological activity in the screening assays.

VII. Isolation of Protease

Processing of full-length alpha-synuclein to the truncated forms of the invention is effected by a protease. The protease can be purified using an inhibitor identified by the screening methods discussed above. A preferred inhibitor is a peptide of alpha-synuclein of e.g., up to 20 contiguous amino acids from SEQ ID NO:1 including residues 114-117, 111-126, 113-126, 113-119, 117-121 or 120-125, or 130-136, 132-138, 131-135, 133-134, 133-137, or 135-136, in which a residue N-terminal to the cleavage site (e.g., between residues 115-116, 119-120, 122-123, 133-134 and 135-136) has been replaced by a transition state analog. Such an inhibitor is used as an affinity purification reagent to purify the protease from extracts of brain cells. Such cells can be obtained from cadaver of a normal individual or one who has suffered from a LBD disease. Levels of protease may be elevated in the latter. The protease can be assayed by presenting it with an alpha-synuclein substrate and monitoring formation of cleavage products. End-specific antibodies described below are useful for detection of cleavage products. The substrate can be, for example, the natural human form of alpha-synuclein described above, a fragment thereof containing residues flanking both sides of the cleavage site, or a mutant form thereof in which the mutation is associated with a hereditary form of LBD. Optionally, the C-terminus of the substrate can be immobilized to the solid phase, and the N-terminus to a label. Cleavage of the substrate releases the label to the liquid phase. The liquid phase can readily be separated from the solid phase, and the amount of label quantified as a measure of proteolytic activity.

VIII. End-Specific Antibodies

The invention provides end-specific antibodies. Such antibodies specifically bind to a truncated form of alpha-synuclein (at the C-terminus), preferably a form selected of the group consisting of SN1-115, SN1-116, SN1-117, SN1-118, SN1-119, 1-120, 1-121, 1-122, 1-123, 1-124, 1-125, 1-126 without specifically binding to full-length alpha-synuclein. Preferred antibodies are end-specific for SN1-115, SN1-119, SN1-122, SN1-133 and SN1-135. Such antibodies are useful for in vivo imaging of alpha-synuclein deposits, as therapeutic agents (see below), and for detecting cleavage products resulting from proteolytic cleavage of alpha-synuclein in the screening methods described above. End-specific antibodies are also provided to corresponding C-terminal fragments, e.g., 116-140, 117-140, 118-140, 119-140, 120-140, 121-140, 122-140, 123-140, 124-140, 125-140, 126-140, 134-140 and 136-140. Preferred fragments are 116-140, 120-140, 123-140, 134-140 and 136-140. The end-specific antibodies recognize the N-terminus of these fragments such that they specifically bind to the fragment without specifically binding to full-length alpha synuclein.

Preferred end specific antibodies are ELADW-101 (polyclonal) and 12C6 (monoclonal) specific for the C-terminus of SN1-119, and ELADW-105 (polyclonal) and 7G8 (monoclonal) specific for the C-terminus of SN1-122. The monoclonals are mouse monoclonals expressed by hybridomas produced by conventional methods.

Such antibodies can be generated by immunizing a laboratory animal with alpha-synuclein or a fragment thereof to induce antibodies, and screening the resulting antibodies to identify those having the desired binding specificity. Optionally, immunization can be performed with relatively short peptides of less than 20 amino acids, usually 7 or 8 amino acids that include the C-terminus of the truncated fragments of the invention (e.g., SN 99-118, SN106-115, SN 110-119, SN-113-122, SN126-133, SN128-135. Optionally, such short peptides are linked to a carrier that helps elicit an immune response. For example, the peptide CGGDMPVD (SEQ ID NO:10) which corresponds to amino acids SN 115-119 with a CGG linker is useful for generating antibodies such as ELADW-101 and 12C6, and the peptide CGGVDPDN (SEQ ID NO:11) which corresponds to amino acids 118-122 with a CGG linker is useful for generating antibodies ELADW-105 and 7G8.

Optionally, specific binding to a labeled or immobilized truncated fragment can be performed in competition with unlabelled full-length alpha-synuclein. Optionally, large libraries of antibodies can be screened simultaneously using the phage display technique.

The production of non-human monoclonal antibodies, e.g., murine, guinea pig, primate, rabbit or rat, can be performed as described by Harlow & Lane, *Antibodies, A Laboratory Manual* (CSHP NY, 1988) (incorporated by reference for all purposes). Complete Freund's adjuvant followed by incomplete adjuvant is preferred for immunization of laboratory animals. Rabbits or guinea pigs are typically used for making polyclonal antibodies. Mice are typically used for making monoclonal antibodies. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to alpha-synuclein. If the test and reference antibodies compete, then they bind to the same epitope or epitopes sufficiently proximal that binding of one antibody interferes with binding of the other.

Chimeric and humanized antibodies have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. In some methods, the isotype of the antibody is human IgG1. IgM antibodies can also be used in some methods. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody, (referred to as the donor immunoglobulin). See, Queen et al., *Proc. Natl. Acad. Sci. USA* 86:10029-10033 (1989), WO 90/07861, U.S. Pat. No. 5,693,762, U.S. Pat. No. 5,693,761, U.S. Pat. No. 5,585,089, U.S. Pat. No. 5,530,101, and Winter, U.S. Pat. No. 5,225,539 (each of which is incorporated by reference in its entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

Human antibodies against alpha-synuclein are provided by a variety of techniques described below. Some human antibodies are selected by competitive binding experiments, or otherwise, to have the same epitope specificity as a particular mouse antibody. Techniques for producing human antibodies include the trioma methodology of Oestberg et al., *Hybridoma* 2:361-367 (1983); Oestberg, U.S. Pat. No. 4,634,664; and Engleman et al., U.S. Pat. No. 4,634,666 (each of which is incorporated by reference in its entirety for all purposes), use of non-human transgenic mammals having-transgenes encoding at least a segment of the human immunoglobulin locus as described by, e.g., Lonberg et al., WO93/1222, U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (each of which is incorporated by reference in its entirety for all purposes) and phage display methods see, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332 (each of which is incorporated by reference in its entirety for all purposes).

The heavy and light chain variable regions of chimeric, humanized, or human antibodies can be linked to at least a portion of a human constant region. The choice of constant region depends, in part, whether antibody-dependent complement and/or cellular mediated toxicity is desired. For example, isotopes IgG1 and IgG3 have complement activity and isotypes IgG2 and IgG4 do not. Choice of isotype can also affect passage of antibody into the brain. Human isotype IgG1 is preferred. Light chain constant regions can be lambda or kappa. Antibodies can be expressed as tetramers containing two light and two heavy chains, as separate heavy chains, light chains, as Fab, Fab° F(ab')2, and Fv, or as single chain antibodies in which heavy and light chain variable domains are linked through a spacer.

In another embodiment, monoclonal antibodies specifically binding to an epitope within residues 109-120, or 115-122, of alpha synuclein, or a discontinuous epitope within residues 43-51 and 58-65, or end-specific to the C-terminus of alpha-synuclein are also provided, including humanized, chimeric and human forms thereof. An end-specific antibody to the C-terminus of alpha-synuclein can be recognized by capacity to specifically bind to alpha-synuclein as a free protein without specifically binding to alpha synuclein as a component of a fusion protein when the C-terminus of alpha-synuclein is linked to a second peptide. These antibodies can be screened for therapeutic activity, and if positive results are obtained, can be used in therapeutic methods. The antibodies can also be used in detecting fragments of alpha-synuclein as described above.

IX. Diagnostics

The invention provides methods of in vivo imaging LBs in a patient. Such methods are useful to diagnose or confirm diagnosis of a Lewy Body disease of PD or susceptibility thereto. For example, the methods can be used on a patient presenting with symptoms of dementia. If the patient has LBs, then the patient is likely suffering from a Lewy Body disease. The methods can also be used on asymptomatic patients. Presence of abnormal deposits of amyloid indicates susceptibility to future symptomatic disease. The methods are also useful for monitoring disease progression and/or response to treatment in patients who have been previously diagnosed with a Lewy Body disease.

The methods work by administering an end-specific antibody as described above that binds to alpha-synuclein in the patient and then detecting the antibody after it has bound. If desired, a clearing response can be avoided by using antibody fragments lacking a full length constant region, such as Fabs. In some methods, the same antibody can serve as both a treatment and diagnostic reagent.

Diagnostic imaging can also be performed using an antibody specific for phosphorylated alpha synuclein, such as the 11A5 (phosphor-specific) or 5C12 (binds to phosphorylated and nonphosphorylated forms of alpha synuclein) monoclonal described in copending application Ser. No. 10/984,192. Presence of phosphorylated alpha synuclein associated with deposits of alpha synuclein is an indication of synucleinopathic disease or susceptibility thereto. Presence of ubiquitinated alpha-synuclein is also a marker of disease. Such can be detected using a two step assay in which alpha-synuclein is precipitated with a first antibody to alpha-synuclein, and the amount of ubiquitinated alpha-synuclein is detected using an antibody to ubiquitin.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for alpha-synuclein is unlabelled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size and/or intensity of labeled loci to corresponding base line values. The base line values can represent the mean levels in a population of undiseased individuals. Base line values can also represent previous levels determined in the same patient. For example, base line values can be determined in a patient before beginning treatment, and measured values thereafter compared with the base line values. A decrease in values relative to base line signals a positive response to treatment.

End-specific antibodies are also useful to determine whether truncated forms of alpha-synuclein are present in cerebrospinal fluid or other body tissues or fluids. Presence of such forms at significantly changed, usually greater, levels (i.e., greater or less than mean plus one standard deviation) in a patient relative to the normal level in a population of undiseased individuals is indicative of presence or susceptibility to a LBD.

X. Methods of Treatment

The invention provides several methods of preventing or treating Lewy Body disease in patients suffering from or at risk of such disease. Therapeutic agents include the truncated forms of alpha-synuclein described above, particularly SN1-115, SN-1-119, SN1-122, SN1-133 and SN1-135 and fragments thereof effective to induce antibodies, end-specific antibodies as described above, and inhibitors of aggregation of truncated fragments of alpha-synuclein or proteolytic processing of alpha-synuclein as described above. Optionally, the fragments are phosphorylated particularly at position 129. Other agents include full-length phosphorylated alpha synuclein, preferably at position 129, agents that inhibit phosphorylation of alpha synuclein, or which promote removal of phosphorylated alpha synuclein by ubiquitination or otherwise, or which promote or inhibit ubiquitination. General approaches for administering agents to patients suffering or at risk of LBD are described in copending application U.S. Ser. No. 60/423,012 filed Nov. 1, 2002, and PCT US00/15239 filed Jun. 1, 2000, and PCT/US03/34527, filed Oct. 31, 2003, each of which are incorporated by reference in their entirety for all purposes, including all references cited therein.

Patients amenable to treatment include individuals at risk of disease of a LBD but not showing symptoms, as well as patients presently showing symptoms. Therefore, the present methods can be administered prophylactically to individuals who have a known genetic risk of a LBD. Such individuals include those having relatives who have experienced this disease, and those whose risk is determined by analysis of genetic or biochemical markers. Genetic markers of risk toward PD include mutations in the alpha-synuclein or Parkin, UCHLI, and CYP2D6 genes; particularly mutations at positions 30 and 53 of the alpha-synuclein gene. Individuals presently suffering from Parkinson's disease can be recognized from its clinical manifestations including resting tremor, muscular rigidity, bradykinesia and postural instability.

In some methods, the patient is free of clinical symptoms or risk factors any amyloidogenic disease other than one characterized by Lewy bodies. In some methods, the patient is free of clinical symptoms or risk factors of any disease characterized by extracellular amyloid deposits. In some methods, the patient is free of diseases characterized by amyloid deposits of Aβ peptide. In some methods, the patient is free of clinical symptoms and risk factors of Alzheimer's disease. In some methods, the patient has concurrent Alzheimer's disease and a disease characterized by Lewy bodies. In some methods, the patient has concurrent Alzheimer's and Parkinson's disease.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to a therapeutic agent (e.g., a truncated form of alpha-synuclein peptide) over time. If the response falls, a booster dosage is indicated.

In prophylactic applications, pharmaceutical compositions or medicaments are administered to a patient susceptible to, or otherwise at risk of a LBD in regime comprising an amount and frequency of administration of the composition or medicament sufficient to eliminate or reduce the risk, lessen the severity, or delay the outset of the disease, including physiological, biochemical, histologic and/or behavioral symptoms of the disease, its complications and intermediate pathological phenotypes presenting during development of the disease. In therapeutic applications, compositions or medicates are administered to a patient suspected of, or already suffering from such a disease in a regime comprising an amount and frequency of administration of the composition sufficient to cure, or at least partially arrest, the symptoms of the disease (physiological, biochemical, histologic and/or behavioral), including its complications and intermediate pathological phenotypes in development of the disease. An amount adequate to accomplish therapeutic or prophylactic treatment is defined as a therapeutically- or prophylactically-effective dose. A combination of amount and dosage frequency adequate to accomplish therapeutic or prophylactic treatment is defined as a therapeutically or prophylatically-effective regime. In both prophylactic and therapeutic regimes, agents are usually administered in several dosages until a sufficient immune response has been achieved. Typically, the immune response is monitored and repeated dosages are given if the immune response starts to wane.

In some methods, administration of an agent results in reduction of intracellular levels of aggregated alpha-synuclein. In some methods, administration of the agent results in a reduction in levels of C-terminal truncated forms of alpha-synuclein. In some methods, administration of an agent results in improvement in a clinical symptom of a LBD, such as motor or cognitive function in the case of Parkinson's disease. In some methods, reduction in intracellular levels of aggregated alpha-synuclein or improvement in a clinical symptom of disease is monitored at intervals after administration of an agent.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

In some methods, the agent is a truncated fragment of alpha-synuclein or a fragment thereof capable of inducing antibodies to alpha-synuclein. The amount of such a fragment depends on whether adjuvant is also administered, with higher dosages being required in the absence of adjuvant. The amount of a fragment for administration sometimes varies from 1-500 μg per patient and more usually from 5-500 μg per injection for human administration. Occasionally, a higher dose of 1-2 mg per injection is used. Typically about 10, 20, 50 or 100 μg is used for each human injection. The mass of fragment also depends on the mass ratio of immunogenic epitope within the fragment to the mass of fragment as a whole. Typically, $10^{-3}$ to $10^{-5}$ micromoles of immunogenic epitope are used for microgram of fragment. The timing of injections can vary significantly from once a day, to once a year, to once a decade. On any given day that a dosage of immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

Truncated fragments of alpha-synuclein can also be administered in the form of nucleic acids encoding the fragments operably linked to one or more regulatory elements to ensure expression of the truncated fragment of alpha-synuclein. Doses for nucleic acids encoding immunogens range from about 10 ng to 1 g, 100 ng to 100 mg, 1 μg to 10 mg, or 30-300 μg DNA per patient. Doses for infectious viral vectors vary from 10-100, or more, virions per dose.

Some methods involve passive immunization with an end-specific antibody. In such methods, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg or, in other words, 70 mg or 700 mg or within the range of 70-700 mg, respectively, for a 70 kg patient. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to alpha-synuclein in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Therapeutic agents can be administered by parenteral, topical, intravenous, oral, subcutaneous, intraarterial, intracranial, intrathecal, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion is preferred for administration of antibody. In some methods, particular therapeutic antibodies are injected directly into the cranium. In some methods, antibodies are administered as a sustained release composition or device, such as a Medipad™ device. Small molecules that act by inhibiting protease processing of alpha-synuclein can be administered intravenously if the small molecules pass through the blood brain barrier sufficiently for therapeutic or prophylactic efficacy or directly into the cranium otherwise.

Agents of the invention can optionally be administered in combination with other agents that are at least partly effective in treatment of LBD. Agents of the invention can also be administered in conjunction with other agents that increase passage of the agents of the invention across the blood-brain barrier.

Immunogenic agents are sometimes administered in combination with an adjuvant. A variety of adjuvants can be used in combination with a peptide, such as alpha-synuclein, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, NY, 1995); U.S. Pat. No. 5,057,540), (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Another adjuvant is CpG (WO 98/40100). Alternatively, alpha-synuclein can be coupled to an adjuvant. However, such coupling should not substantially change the conformation of alpha-synuclein so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipamitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+CWS (Detox™).

Another class of preferred adjuvants is saponin adjuvants, such as Stimulon™ (QS-21, Aquila, Framingham, Mass.) or particles generated there from such as ISCOMs (immunostimulating complexes) and ISCOMATRIX. Other adjuvants include RC-529, GM-CSF and Complete Freund's Adjuvant (CFA) and Incomplete Freund's Adjuvant (IFA). Other adjuvants include cytokines, such as interleukins (e.g., IL-1, IL-2, IL-4, IL-6, IL-12, IL13, and IL-15), macrophage colony stimulating factor (M-CSF), granulocyte-macrophage colony stimulating factor (GM-CSF), and tumor necrosis factor (TNF). Another class of adjuvants is glycolipid analogues including N-glycosylamides, N-glycosylureas and N-glycosylcarbamates, each of which is substituted in the sugar residue by an amino acid, as immuno-modulators or adjuvants (see U.S. Pat. No. 4,855,283). Heat shock proteins, e.g., HSP70 and HSP90, may also be used as adjuvants.

An adjuvant can be administered with an alpha-synuclein fragment as a single composition, or can be administered before, concurrent with or after administration of the alpha-synuclein fragment. The alpha-synuclein fragment and adjuvant can be packaged and supplied in the same vial or can be packaged in separate vials and mixed before use. The alpha-synuclein fragment and adjuvant are typically packaged with a label indicating the intended therapeutic application. If the alpha-synuclein fragment and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, MPL or RC-529 with GM-CSF, and alum, QS-21 and MPL together. Also, Incomplete Freund's adjuvant can be used (Chang et al., *Advanced Drug Delivery Reviews* 32, 173-186 (1998)), optionally in combination with any of alum, QS-21, and MPL and all combinations thereof.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl. Compositions for parenteral administration are typically substantially sterile, substantially isotonic and manufactured under GMP conditions of the FDA or similar body.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein. Alternatively, transdermal delivery can be achieved using a skin path or using transferosomes (Paul et al., *Eur. J. Immunol.* 25, 3521-24 (1995); Cevc et al., *Biochem. Biophys. Acta* 1368, 201-15 (1998)).

EXAMPLES

1. Detecting Truncated Forms of Alpha-Synuclein in a Transgenic Animal

Transgenic mice having a nucleic acid encoding intact alpha-synuclein operably linked to a PDFG promoter were analyzed at 6 weeks, 3 months and 12 months old. The animals were euthanized and the cortex and hippocampus tissue from four mice (2 male/2 female) was pooled. The tissue was homogenized in TBS (250 mM NaCl), and spun at 150,000×g for 15 minutes. The pellet was then extracted with 1% Triton-X 100 for 30 min at 4 degrees and spun as before. The resulting pellet was then extracted with 1% SDS for 30 min at 25 degrees and spun as before. Finally, the pellet was extracted with 8 M Urea/1% SDS. This procedure resulted in four extracts which will be referred to as Tris, Triton, SDS, and Urea extracts in the description that follows.

FIGS. 1A and B show a Western blot of extracts from a transgenic mouse and a matched control with antibody ELADW-47. This antibody is a polyclonal that binds to an epitope within SN115-122 (but does not necessarily require each amino acid for some binding to occur). The antibody preferentially binds the human form of alpha-synuclein but also binds the mouse form to a lesser extent. FIGS. 1A and B shows an alpha-synuclein band at 14 kDa for both the control mouse and the transgenic mouse. The band is stronger for the transgenic mouse than the control. For the different extracts, the band is most intense in the Triton extract. This extract solubilizes membrane bound alpha-synuclein and possibly Lewy body-like inclusions. The Tris and particularly the Triton extractions of the transgenic mouse (but not the control) show a band at about 12 kDa in a tricine buffer. This is a truncated form of alpha-synuclein. The molecular weight of the band corresponds to a length of about 115-120 amino acids.

Figure 2:
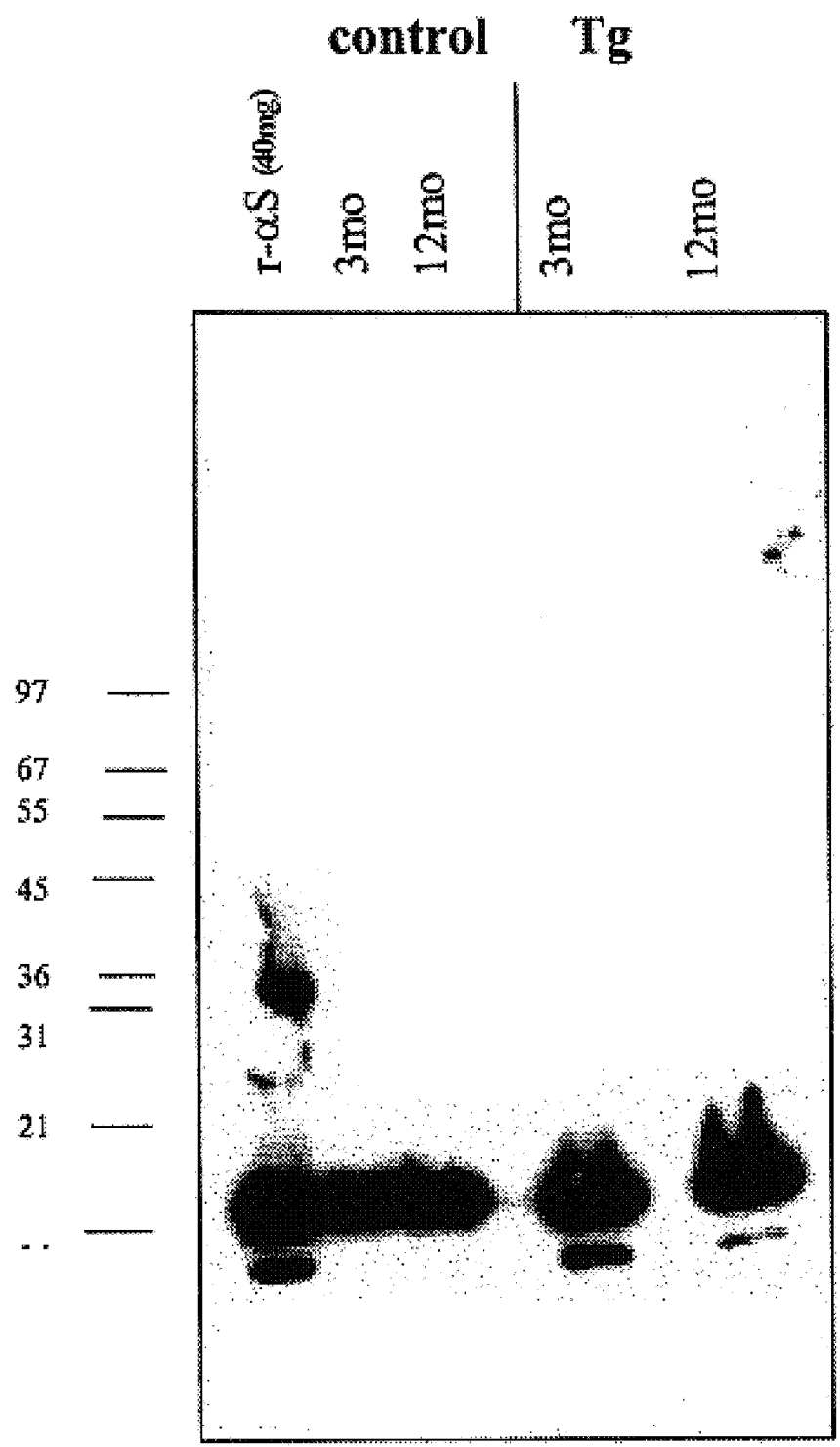
FIG. 2 shows a Western blot with the same antibody as FIGS. 1A and B to compare the level of the truncated form of alpha-synuclein in Triton-X100 extractions of the cortex and hippocampus mice of 3 months and 12 months in age.

FIG. 2 shows a Western blot with the same antibody as FIGS. 1A and B to compare the level of the truncated form of alpha-synuclein in mice of 3 months and 12 months in age. The Figure shows that the truncated form appears more strongly in the 3 month old mice. Again, the truncated band does not appear in the control mice. The more intense appearance of the truncated form of alpha-synuclein early in development of the transgenic mice indicates that the truncated form of alpha-synuclein has a role early in the pathogenesis of Lewy Body disease.

Figure 3A:
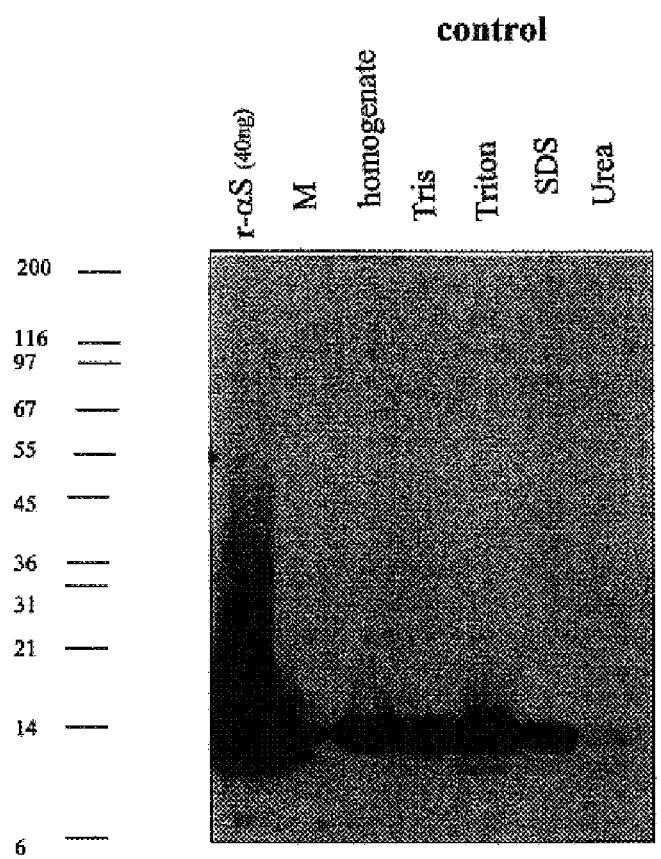
FIGS. 3A and B shows a Western blot with a different antibody termed 12C1 (a monoclonal binding to epitope at amino acids 43-51 and 58-65) of a Triton extracts from the brain of a transgenic mouse three months old (B) compared with an aged matched control (A).
Figure 3B:
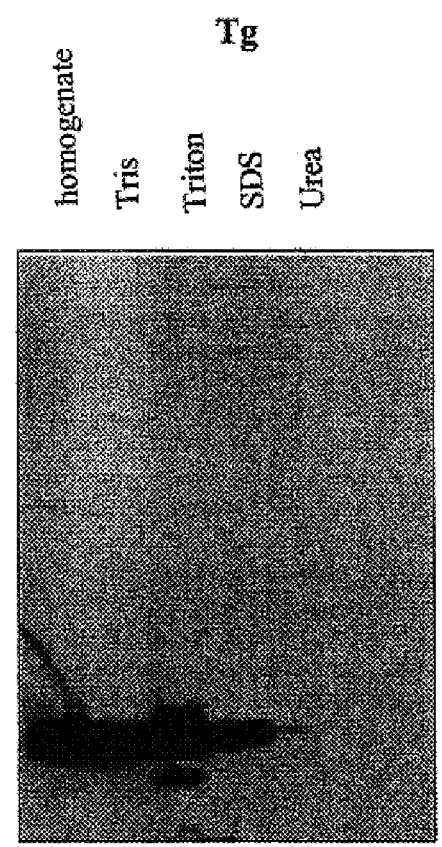

FIGS. 3A and B show a Western blot with a different antibody termed 12C1 (binds epitope at amino acids 43-51 and 58-65, monoclonal, IgG1 k). This antibody binds equally to mouse and human forms of alpha-synuclein at an epitope including amino acids 43-51 and 58-65. FIG. 3 shows the truncated band of 12 kDa in the Triton extract of the transgenic mice. The same band appears much more faintly in the Triton extract of the control mice. Thus, processing of alpha-synuclein to a truncated form occurs in both normal mice and transgenic mice, but more strongly in the latter. The greater extent of processing in the transgenic mice may be due to processing of the human alpha-synuclein directly, or may be due to the presence of human alpha-synuclein driving mouse alpha-synuclein down a path that is used to a lesser extent in nontransgenic mice.

Figure 4:
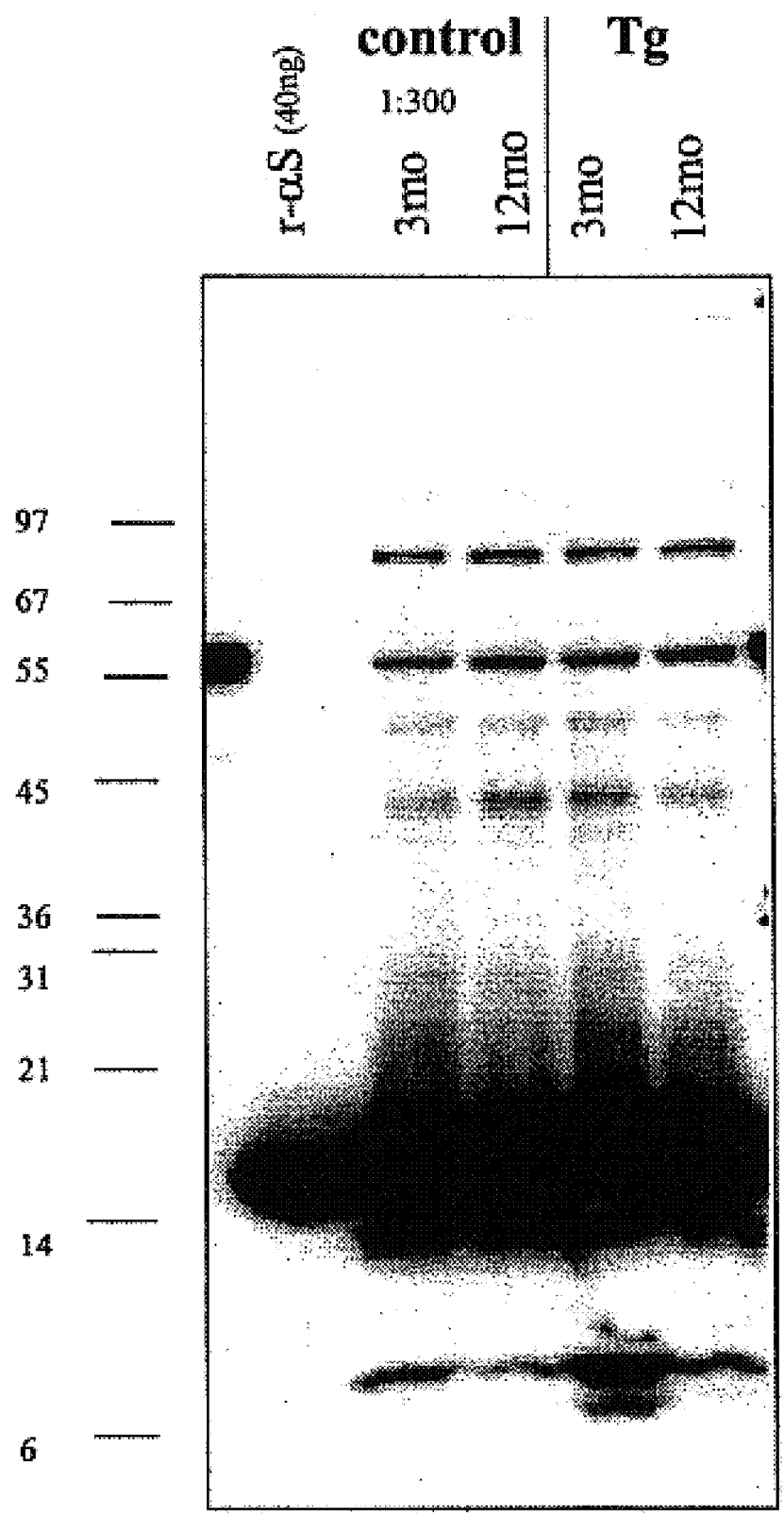
FIG. 4 shows a further Western blot using the same antibody as FIG. 3 on a Triton extract from the brain of transgenic mice of three and twelve months of age.

FIG. 4 shows a further Western blot using the same antibody as FIG. 3. This gel shows two additional bands of molecular weights approximately 6 or 7 kDa. The 7 kDa band appears more strongly in the transgenic mice than control mice. The 6 kDa band appears only in the transgenic mouse, and then only in the 3 mo sample. The 6 or 7 kDa bands are indicative of shorter N-terminal fragments of alpha-synuclein of length about 50-80 amino acids.

Figure 5A:
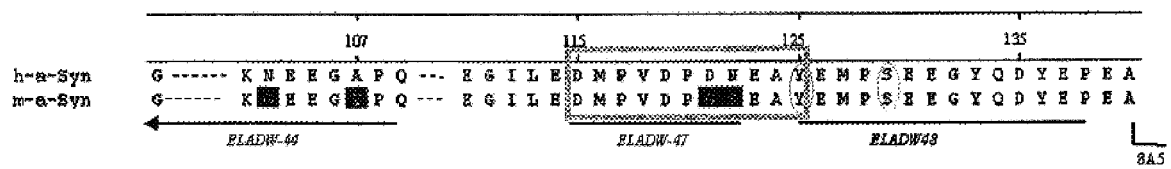
FIGS. 5A, B, C, D, E show Western blots with four different antibodies (B, C, D, E) and an epitope map (A)(SEQ ID NOS:5-8) of the binding sites of the antibodies to various extracts from the brains of transgenlc mice.
Figure 5B:
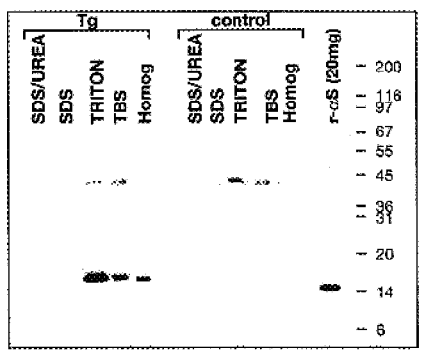
Figure 5D:
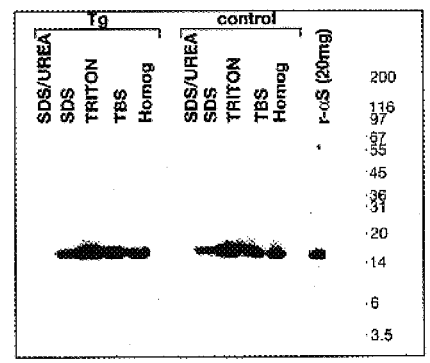
Figure 5C:
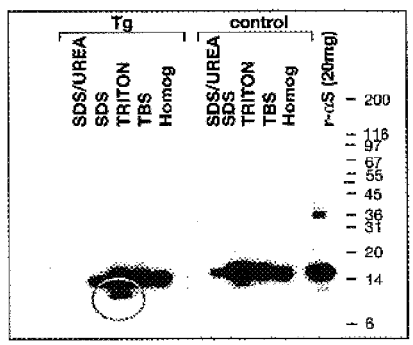
Figure 5E:
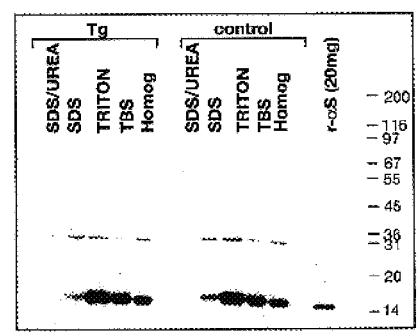

FIGS. 5A, B, C, D, E shows Western blots with four different antibodies and epitope maps of the binding sites of the antibodies. ELADW-44 is a polyclonal that binds only to the human form of alpha-synuclein (i.e., not the mouse form) It binds to at epitope at amino acids 103-105. ELADW-47 is a polyclonal that binds preferentially to the human form but also binds the mouse form. It binds to an epitope at amino acids 115-122. ELADW-48 is a polyclonal that binds the human and mouse forms equally. It binds to an epitope between amino acids 131 and 140. 8A5 is a monoclonal that binds to the human and mouse forms equally. It binds to the C-terminus of alpha-synuclein. FIGS. 5A-E shows that of these four antibodies, only ELADW-47 generated a 12 kDa band indicative of a truncated form of alpha-synuclein. The result that ELADW48 did not give rise to this band is of assistance in mapping the site of cleavage. Because ELADW-47 did bind and ELADW-48 did not, the site of cleavage is bordered by the N-terminal end of the ELADW-47 epitope and the C-terminal amino acid of the ELADW48 epitope. Further, because some amino acids from the ELADW-47 epitope must be present to allow binding and some of the ELADW-48 epitope must be absent to prevent binding, the cleavage site is further confined to a region approximately within amino acids 118-135. When this data is considered with the size of the truncated fragment (about 115-120 amino acids) then the probable site of cleavage is around amino acids 118-121. The lack of binding by the C-terminal antibody 8A5 is consistent with this cleavage site. The lack of binding by the antibody ELADW-44, however, requires further comment. The lack of cleavage can be explained if a truncated form of human alpha-synuclein resulting from cleavage adapts a different conformation to intact alpha-synuclein preventing binding of ELADW-44. Alternatively, the truncated form of alpha-synuclein present in transgenic mice to a greater extent than in normal mice represents a form of mouse alpha-synuclein. In this case, the greater amount of the truncated form in the transgenic mouse would be due to the presence of the human alpha-synuclein driving more of the mouse alpha-synuclein down a processing path that leads to truncated alpha-synuclein relative to the situation in a control mouse.

2. Detecting Truncated Forms of Alpha-Synuclein in the Brain of a Patient with DLBD This example compares alpha-synuclein species in LBs to those in the remaining soluble and particulate protein fractions of a DLBD brain. LBs and soluble protein were prepared from the cortex of a single DLBD patient (see Jensen et al., *J. Biol. Chem.* 275 21500-21507 (2000)). Tissue was homogenized in Tris/sucrose (0.32 mM)/EDTA (5 mM) and protease inhibitors buffer. The homogenate was spun at 1000×g. The supernatant was subjected to a further spin at 150,000×g. The supernatant from this spin was used to prepare a Tris soluble fraction of proteins. The pellet from the 1000×g was resuspended and used to prepare a Lewy body fraction. Lewy bodies were purified by immunoprecipitation on magnetic beads bearing anti-synuclein antibodies. The precipitate was then extracted with 7 M Urea/2 M Thiourea/4% CHAPS. The unextracted material was reextracted with Urea/Thiourea/CHAPS. The extracts from this step and the previous extraction were then pooled and analyzed by 2D PAGE and immunoblot. The unextracted residue was subject to further extraction with 90% formic acid. This extract was stored diluted to 9% formic acid. The extract was then analyzed by SDS PAGE and RP-HPLC. Little or no synuclein was found in this last extract, and what was present resembled the material extracted by Urea/Thiourea/CHAPS, indicating that the Urea/Thiourea/CHAPS gave a comprehensive extraction.

Synuclein species were resolved on 2-D gels and detected on Western blots. All 2D Western blots are shown with more acidic proteins on the left, more basic on the right. Multiple alpha-synuclein species, including phosphorylated and truncated species, were present in both LBs and the soluble brain fraction. The predominant truncations were in the C-terminal region of alpha-synuclein at approximately amino acids 118-125. An additional larger fragment cleaved close to the C-terminus was also observed. No beta or gamma-synuclein was detected in the LBs despite being found in the soluble protein fraction. The alpha-synuclein in the LB preparation differed from that in the soluble fraction in that it had additional C-terminal cleavages, and that overall the truncated alpha-synuclein species were enriched in the LBs relative to the soluble protein fraction. In addition, multiple alpha-synuclein species of higher molecular mass, approximately 25-35 kDa, were detected only in the LB preparation. These include ubiquitinated species, as identified by us and by others (Tofaris et al. J. Biol. Chem. 278(45): 44405-44411, 2003). The C-terminally truncated fragments are of the same size as those observed in the transgenic mouse model of Example 1 indicating a role in disease pathogenesis.

Figure 6A:
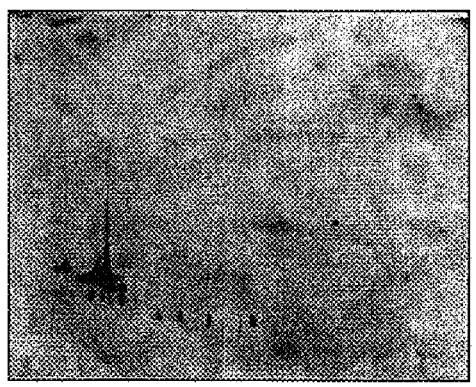
FIGS. 6A, B, C shows Tris extracts of the brain of a patient with Lewy body disease probed with three different antibodies (A, B, C), subject to 2-D gel electrophoresis and subjected to Western blotting. All 2D gels in this document are shown with acidic proteins on the left, more basic proteins on the right.
Figure 6B:
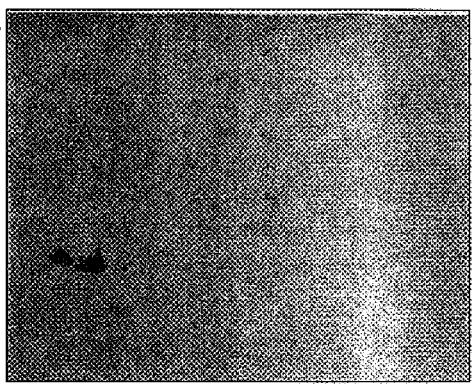
Figure 6C:

FIGS. 6A, B, C shows Tris extracts probed with different antibodies, subject to 2-D gel electrophoresis and subjected to Western blotting. The dark spots present toward the left of the charts represent full-length alpha-synuclein. The most notable feature is four spots in the Syn-1 chart that are absent in the 8A5 chart. These four spots represent truncated forms of alpha-synuclein that are unable to bind the 8A5 antibody because of the lack of a C-terminal amino acid. These truncations correspond approximately to forms of SN between 1-118 and 1-125. Several additional spots are seen underneath and adjacent to the full length alpha-synuclein spots. The spots underneath the full length spots probably represent minor truncations from the C-terminus (i.e., synuclein 1-X, wherein X is 130-139), since they react with antibodies to phosphorylated S129 but not with 8A5. The spot adjacent the full-length spots but to the right represent a minor deletion from the N-terminus (due to lack of this spot in the blot with ELADW43).

Figure 7A:
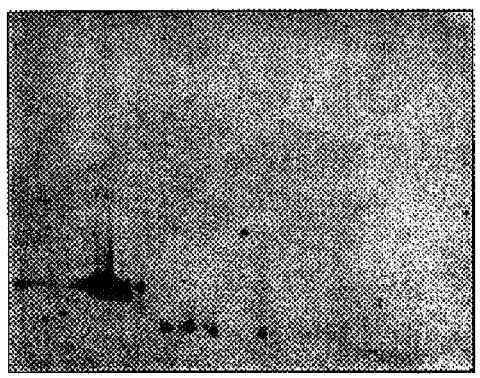
FIG. 7A, B, C, D shows additional blots of Tris extracts of the brain of a patient with Lewy body disease with four antibodies (A, B, C, D) of additional specificities.
Figure 7C:
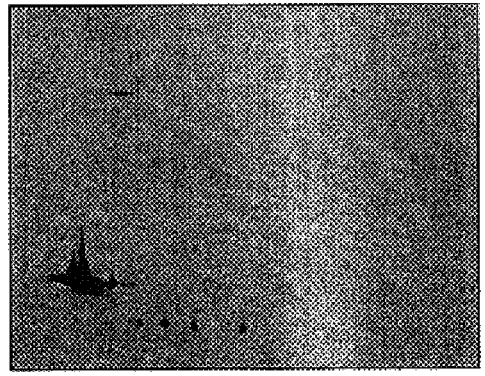
Figure 7B:
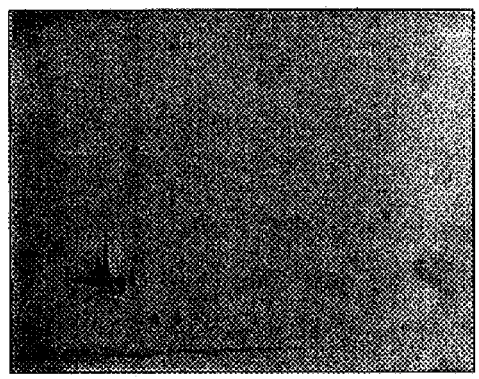
Figure 7D:
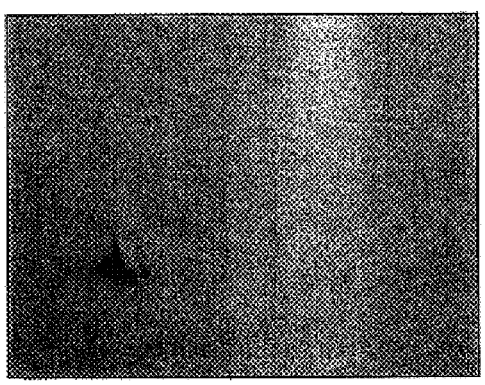

FIGS. 7A, B, C, D shows blots with additional antibodies. The four spots are present with 5C12 (111-118). Two of the spots are present with ELADW47 (115-122) and the spots are absent with LB509 (115-123). The spots may differ from each other both in molecular weight and in the presence or absence of posttranslational modification, such as nitration or phosphorylation. The shift of these fragments towards a basic pH, relative to the full length synuclein, is consistent with removal of a portion of the acidic C-terminal sequence. These results fix the sites of cleavage to within about amino acids 120-125 of alpha-synuclein. Also notable are several spots running slight below (lower molecular weight) or to the left (lower pH) than the unmodified synuclein spots. These likely may represent forms of synuclein that have undergone a small extent of N-terminal truncation and/or different posttranslational modification relative to the main spots. Note that some spots visualized by ELADW43 and 8A5 in the blots of soluble protein are beta synuclein, particularly the prominent spot to the left and slightly above the full length alpha.

Figure 8:
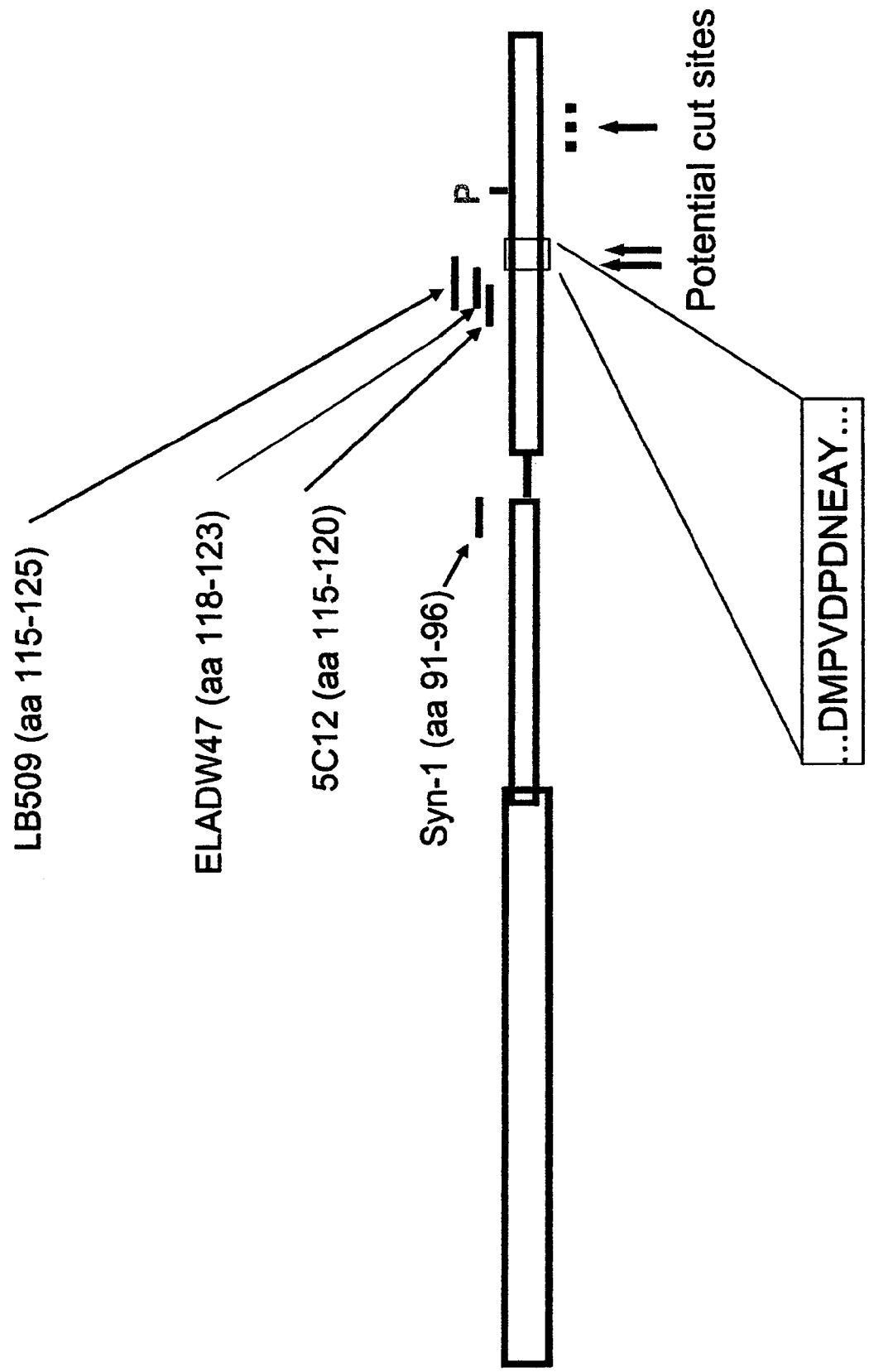
FIG. 8 summarizes the sites of cleavage (SEQ ID NO:9) relative to the epitopes bound by antibodies used in the Western blotting.

FIG. 8 summarizes the sites of cleavage relative to the epitopes bound by antibodies used in the Western blotting.

Figure 9A:
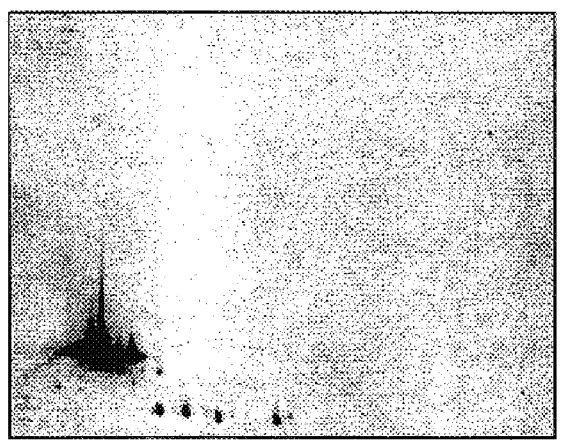
FIGS. 9A, B compares the Tris soluble proteins (A) with proteins extracted from Lewy bodies (B) by 2D electrophoresis and Western blotting.
Figure 9B:
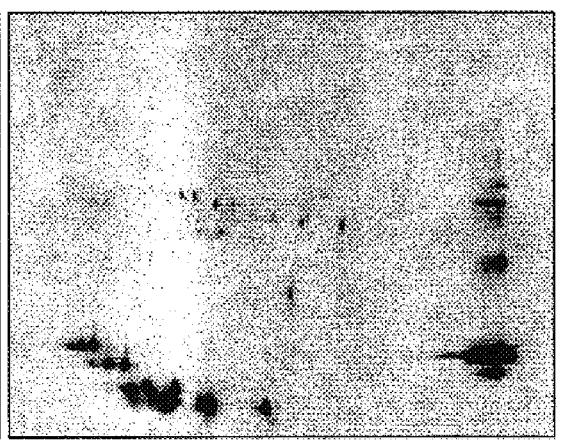

FIGS. 9A, B compare the Tris soluble proteins with proteins extracted from Lewy bodies by 2D electrophoresis and Western blotting. The Tris blot on the left shows four spots at lower molecular weight representing truncated forms of alpha-synuclein (probably in the 1-120 to 1-125 amino acid range). These are of relatively low intensity compared to the spots representative of full length alpha-synuclein. The blot of proteins from Lewy bodies shows more spots representative of truncated forms of alpha synuclein in the 1-120 to 1-125 range. However, these are of greater intensity relative to the spots representative of full length alpha synuclein. Also, apparent are two spots migrating faster than full-length alpha synuclein but slower than the collection of spots at the bottom of the blot. These spots probably represent truncations in the range 1-X wherein X is 130-139 amino acids. As above, these spots react with antibodies to phosphorylated S129 but not with 8A5.

Figure 10A:
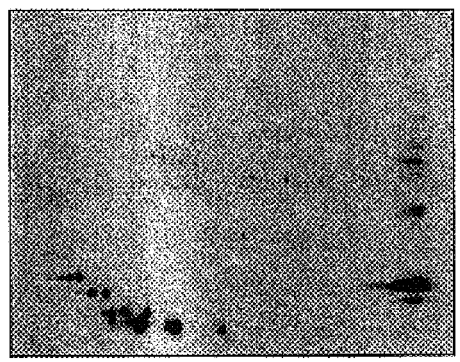
FIGS. 10A, B, C, D show the immunoblots of proteins from Lewy bodies reprobed with various C-terminal antibodies.
Figure 10C:
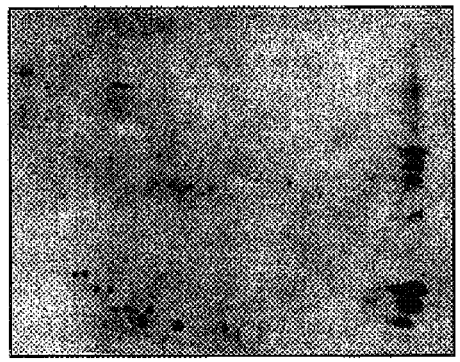
Figure 10B:
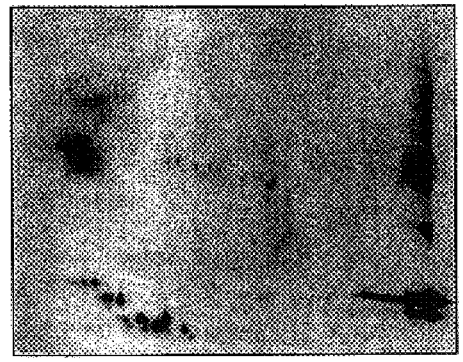
Figure 10D:
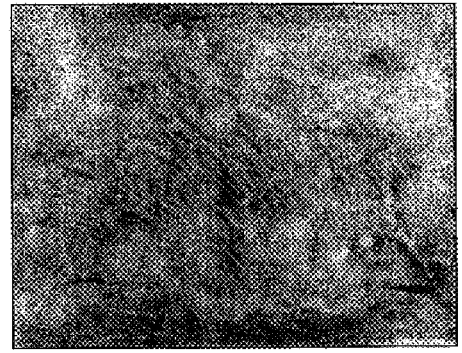

FIGS. 10A, B, C, D show the immunoblots of proteins from Lewy bodies reprobed with various C-terminal antibodies. All spots appear with Syn-1 (91-96) and 5C12 (111-118). With ELADW47, the spot running at the fastest speed and most basic position in the Syn-1 and 5C12 blots is missing. In the LB509 blot, the 12 kD spots corresponding to those in the Tris soluble samples are missing or faint, although the row of spots just above them ("tier 3") still react. The absence or reduced intensity of certain spots in the ELADW47 and LB509 blots indicates that these spots represent truncated forms of alpha-synuclein and are consistent with cleavage occurring approximately between amino acids 120 and 125.

3. Detecting Aggregated Alpha-Synuclein in a Transgenic Animal

Transgenic animals are euthanized and brains are removed for neurochemical and neuropathological analysis Briefly, the right hemibrain is frozen and homogenized for determinations of aggregated and non-aggregated human alpha-synuclein immunoreactivity by Western blot (Masliah et al., *Science* (2000) 287:1265). The left hemibrain is fixed in 4% paraformaldehyde, serially sectioned in the vibratome for immunocytochemistry and ultrastructural analysis.

Brain sections are immunostained with a rabbit polyclonal antibody against human alpha-synuclein (1:500). After an overnight incubation at 4° C., sections are incubated with biotinylated anti-rabbit secondary antibody followed by Avidin D-Horseradish peroxidase (HRP) complex (1:200, ABC Elite, Vector). The reaction is visualized with 0.1% 3,3,-diaminobenzidine tetrahydrochloride (DAB) in 50 mM Tris-HCl (pH 7.4) with 0.001% $H_2O_2$ and sections are then mounted on slides under Entellan. Levels of immunoreactivity are semi quantitatively assessed by optical densitometry using the Quantimet 570C. These sections are also studied by image analysis to determine the numbers of alpha-synuclein immunoreactive inclusions and this reliable measure of alpha-synuclein aggregation acts as a valuable index of the anti-aggregation effects (Masliah et al. *Science* (2000) 287:1265).

Analysis of patterns of neurodegeneration is achieved by analyzing synaptic and dendritic densities in the hippocampus, frontal cortex, temporal cortex and basal ganglia utilizing vibratome sections double-immunolabeled for synaptophysin and microtubule-associated protein 2 (MAP2) and visualized with LSCM. Additional analysis of neurodegeneration is achieved by determining tyrosine hydroxylase (TH) immunoreactivity in the caudoputamen and substantia nigra (SN) as previously described (Masliah, et al. (2000)). Sections will be imaged with the LSCM and each individual image is interactively thresholded such that the TH-immunoreactive terminals displaying pixel intensity within a linear range are included. A scale is set to determine the pixel to μm ratio. Then, this information is used to calculate the % area of the neuropil covered by TH-immunoreactive terminals. These same sections are also utilized to evaluate the numbers of TH neurons in the SN.

4. Analysis of Alpha-Synuclein in LBD Patients

Figures 11A, 11B:
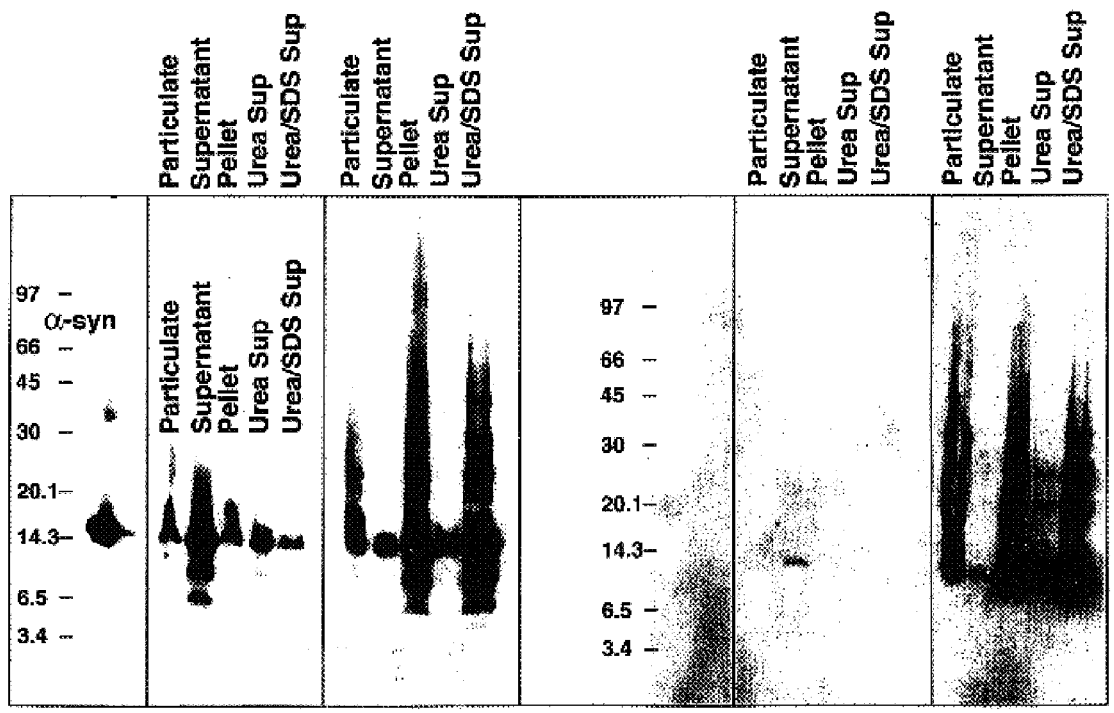
FIGS. 11A, B show Western blots of various extracts of an undiseased and Contursi patient probed with an antibody recognizing either total alpha synuclein (A) or specific for phospho-129 alpha synuclein (B).

To determine which species of α-synuclein are enriched in or unique to disease tissue, we have examined brain samples from patients with multiple system atrophy (MSA) and a familial Parkinson's disease mutation (A53T; Contursi kindred). Particulate fractions of MSA and Contursi brain were prepared by homogenizing brain tissue in 50 mM Tris, 140 mM NaCl and 1% Triton respectively Age matched, control patients ("normals") were prepared identically to the disease brain. Samples were analyzed on western blots of 1-D gels and by ELISA as described below, and also on 2-D gels. Part of the particulate fraction was analyzed. The rest was spun. The supernatant was also analyzed. The pellet was extracted in 7 M urea. The supernatant from this extraction was analyzed. The pellet was further extracted in 7 M urea/1% SDS. The supernatant was analyzed. Western blots using an antibody to detect total alpha-synuclein or to specifically alpha-synuclein phosphorylated at position 129 are shown in FIGS. 11A and B.

The synuclein fractionated differently from the particulate fraction of the Contursi brain versus control brain. Most of the synuclein in the particulate fraction of the normal brain was soluble after homogenization in tris buffered sucrose but almost all of the synuclein in the Contursi brain required urea plus SDS for solubilization suggesting a massive amount of Lewy bodies in this patient. The synuclein in the Contursi patient was strikingly different from that in the control patient in the amount of ser 129 phosphorylation. Only a small amount of phosphorylated α-synuclein was detected in the control patient (left tracks), whereas the Contursi patient (right tracks) had an extremely large amount of phospho-synuclein by comparison on western blots. Thus, the insolubility of synuclein in the Contursi brain was associated with a large increase in synuclein phosphorylation at ser 129. The α-synuclein in the Contursi patient also differed from that in normal brain in the distribution of C-terminal truncations. C-terminally truncated α-synuclein were observed in both control and Contursi particulate brain fraction However, all detectable truncations were highly insoluble (urea/SDS extract) in the Contursi patient, whereas those in the control brain were soluble (tris buffered sucrose extract). The enrichment of the C-terminally truncated synuclein in a LB-enriched fraction of a Contursi patient is in agreement with our finding of C-terminally truncated synuclein enrichment in DLBD LBs. The MSA brain was also enriched in phospho (ser 129)-α-synuclein revealed C-terminal truncation and an abundance of phosphorylation and other acidic modifications also seen in LBs. High levels of phospho (ser 129) were also seen in the brain of a DLBD patient relative to an undiseased control.

5. Identification of Truncated Synuclein Species from DLBD Brain by LC-MS/MS

To generate an enriched pool of α-synuclein, a Urea/Thiourea/CHAPS solubilized particulate fraction of DLBD brain was first purified by anion exchange chromatography. The resulting fractions were analyzed by Western Blot and separated into crude pools enriched in truncated, full length, or phospho-synuclein. The truncated pool was further purified by affinity chromatography (5C12 antibody conjugated to Sepharose). Next, individual fractions were individually concentrated and separated by capillary HPLC.

The three major peaks from one fraction (designated C6) were subsequently digested with trypsin and analyzed by LC-MS/MS to determine the identity and composition of the protein present in the sample. Peak 1 was analyzed and α-synuclein was identified with sequence coverage spanning amino acids 1-97. Since the sequence coverage ends at the C-terminus with a lysine residue, which is a trypsin cleavage site, additional downstream peptides may be present.

Peak 2 from fraction C6 was analyzed and found to contain α-synuclein sequence from positions 11-97. Again, since tryptic fragments on both the N and C termini are absent; the exact composition of the species is not able to be determined. Also, the majority of the protein present in this fraction is not synuclein, but a form of myelin basic protein that co-purified with this synuclein pool.

Figure 12:
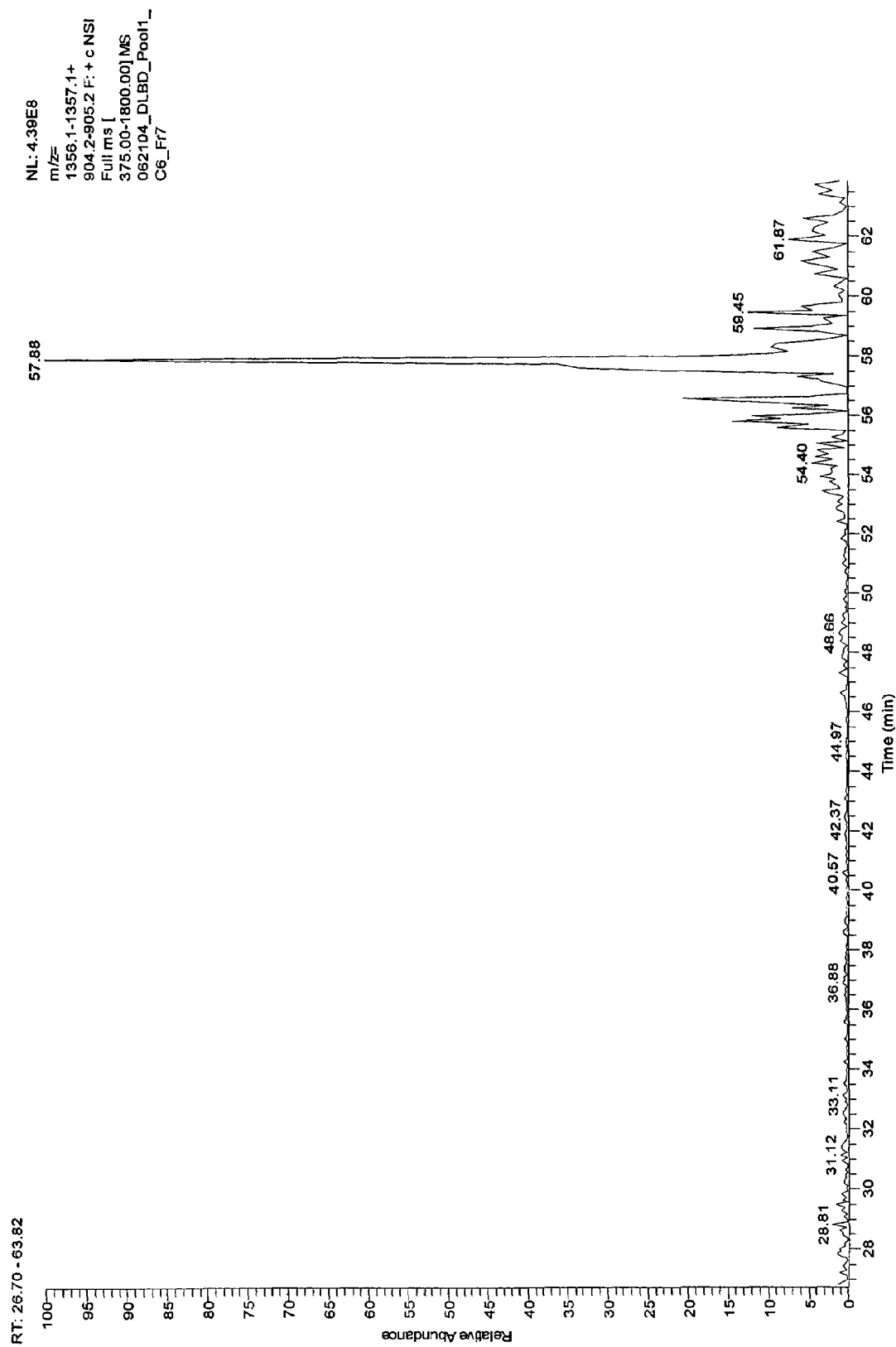
FIG. 12 Extracted ion chromatogram of C-terminal peptide of SN1-122.
Figure 13:
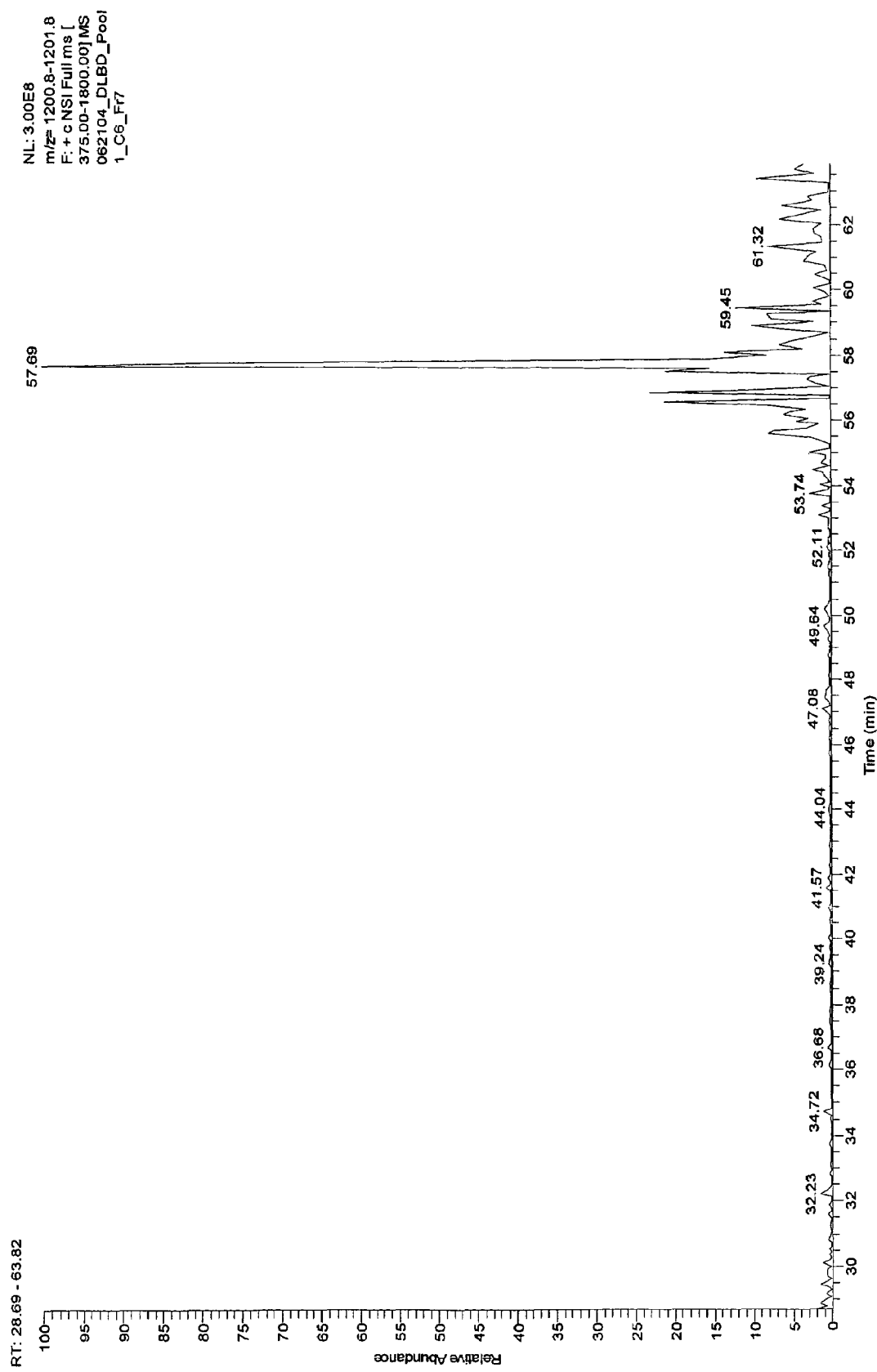
FIG. 13: Extracted ion chromatogram of C-terminal peptide of SN1-119.

Analysis of Peak 3 identified two different synuclein species, both beginning at amino acid 1, with one terminating at position 119D and the other at position 122N. Both of these truncated forms were identified using a database search designed to detect truncated C-terminal tryptic peptides. The database search results listing the truncated C-terminal peptide fragments are shown below (Table 1) along with their respective extracted ion chromatograms (FIGS. 12 and 13) which illustrate the intensity of the precursor (unfragmented) ion signals for these peptides when compared to baseline level.

TABLE 1

Database search results for Fraction-C6 Peak 3

| Reference Scan(s) | Sequence | MH+ | Charge | XCorr |
|---|---|---|---|---|
| #2 alpha_synuclein(C122) | | | | |
| 2690-2694 (SEQ. ID NO: 2) | DQLGKNEEGAPQEGILEDMPVDPDN. | 2710.22 | 2 | 4.53 |
| 2344-2679 | KDQLGKNEEGAPQEGILEDMPVDPDN. | 2838.31 | 3 | 2.38 |

TABLE 1-continued

Database search results for Fraction-C6 Peak 3

| Reference Scan(s) | Sequence | MH+ | Charge | XCorr |
|---|---|---|---|---|
| (SEQ. ID NO: 3) #3 alpha_synuclein(C119) 2675 (SEQ. ID NO: 4) | KDQLGKNEEGAPQEGILEDMPVD. | 2512.19 | 2 | 1.94 |

The search identified the 122N truncation twice, finding two different tryptic sequences for the 122N species, with one peptide being the result of a missed tryptic cleavage of the N-terminal lysine residue. Also, the Xcorr, or cross correlation score, for the first listed sequence of the 122N variant is very high. Three additional truncated forms SN1-115, SN1-133 and SN1-35 have also been found in DLBD brains. Truncations were identified by matching MS/MS peptide fragmentation spectra from the truncated C-terminal a-synuclein peptides against a theoretical spectrum generated by TurboSequest Mass spectral analysis software (licensed from ThermoElectron, Inc). Both forms were phosphorylated at Ser129. The greater the Xcorr value, the higher the confidence in the match, which lends more support to the data.

Figure 14A:
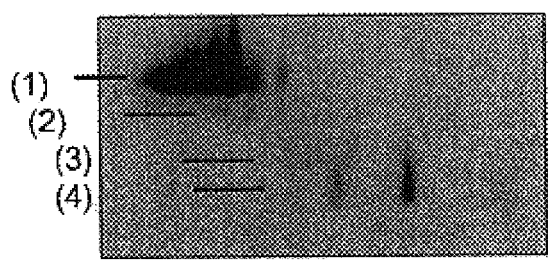
FIGS. 14A, B, C, D, E and F: 2D immunoblot with antibody recognizing total synuclein. Dashes mark positions of four rows of C-truncated synuclein species.
Figure 14D:
FIG. 14D is a control.
Figure 14B:
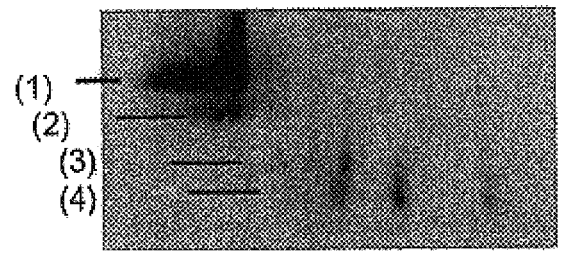
Figure 14E:
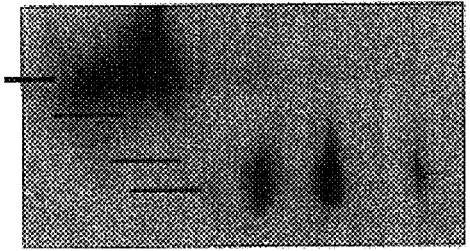
Figure 14C:
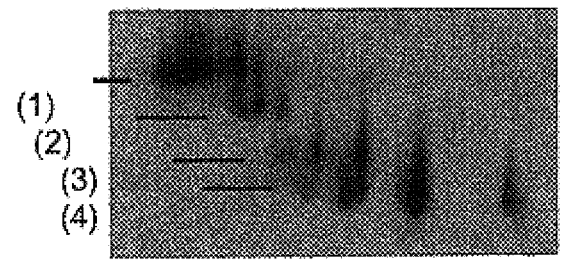
Figure 14F:
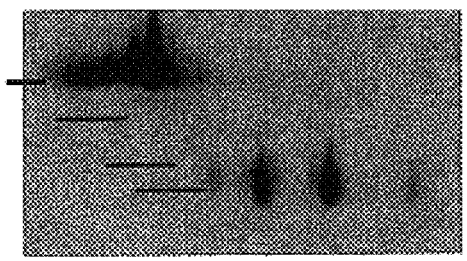
Figure 15A:
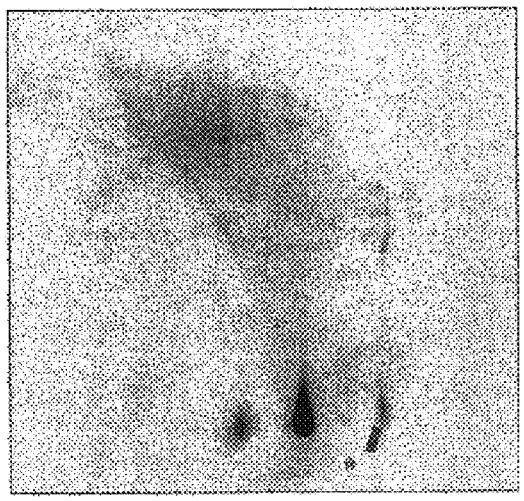
FIGS. 15A, B: 2D immunoblots comparing ELADW101 (B), which is end specific for SN1-119 with an antibody to total alpha synuclein (A). Asterisks indicate spots which react with both antibodies. These spots are identified as SN1-119.
Figure 15B:
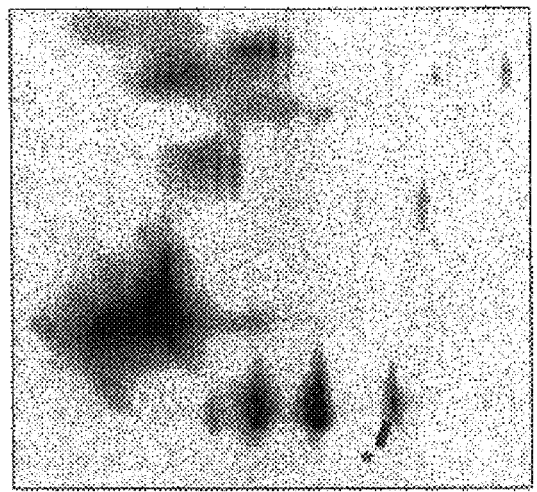

FIGS. 14A-F show immunoblots of 2D gels of extracts of Lewy body preparations from DLB patients P48 and P52 and MSA patient P2 (strictly speaking, the MSA preparation contains glial cortical inclusions) prepared as above compared with a control. The probe is antibody to total alpha synuclein. The identifying numbers (A/1, U/1, etc.) refer to different Lewy body preparations, done on different days and using different cortical regions. Different preparations from diseased patients are shown in FIGS. 14A, B, C, E and F. The control is shown in FIG. 14D. No synuclein modifications were consistently present or absent in the MSA preparation compared to those from DLB, so the two pathologies will be discussed together. Most preparations have the same groups of adducts migrating above full-length synuclein monomer although the relative amount of each group varies. The C-truncated synuclein between 16 and 12 kD can be grouped into four tiers, ranging from full-length in the first tier to the 12 kD fragment in the fourth. The relative amounts of the different truncations vary. P52U/2 and P28U/1 have none of the DLB-specific tier 3 detectable. P48 has very little C-truncated material; its tier 3 spots are barely visible (although present), and the tier 4 is not much more intense, if at all, than the soluble proteins. FIG. 15B shows the results of reprobing a 2D immunoblot of the P52U/2 Lewy body preparation with ELADW101. A previous probe of the same blot with the monoclonal Syn-1 is shown to the left for comparison (FIG. 15A). Three asterisks mark spots that overlay each other on the two probes. The P28U/1 blot was also reprobed with identical results. The polyclonal antibody ELADW101, directed against termination at Asp119, specifically reacts with the 3 most prominent spots in the 12 kD fourth row of truncated species The multiple spots suggest different forms of SN1-119 differing by charge modifications, e.g. phosphorylation, of the remaining sequence.

Figure 18A:
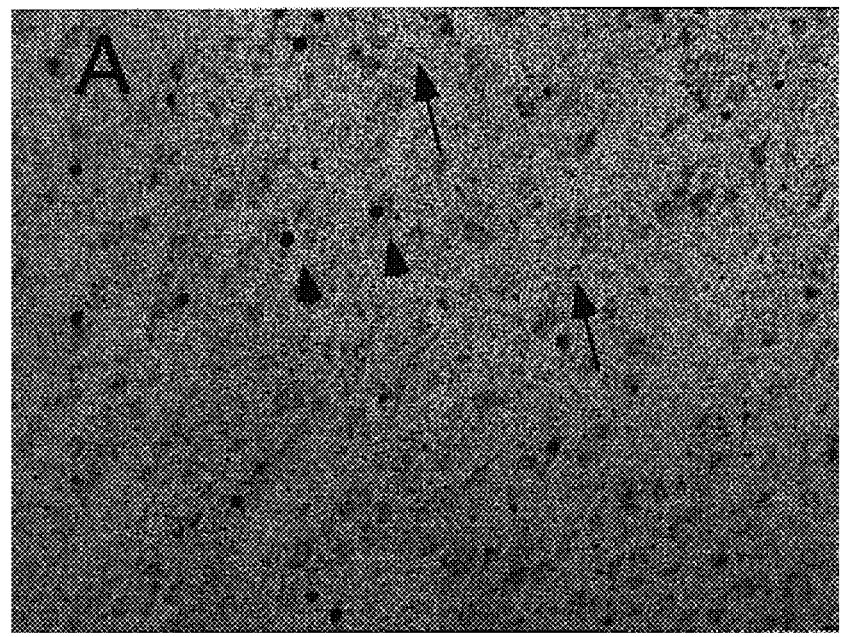
FIGS. 18A and B are brain sections from a DLBD patient stained with SN1-119 end-specific monoclonal antibody 12C6.
Figure 18B:
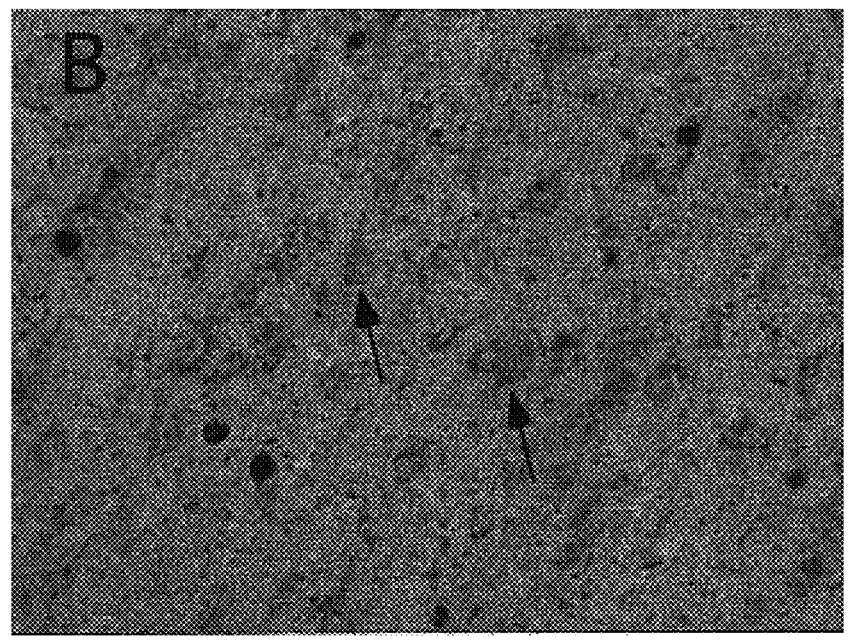

Free-floating, cortical brain sections from a normal and DLBD patient were probed with the neo-epitope specific antibody ELADW-101. The results are shown in FIGS. 16A and B (diseased brain) and FIGS. 17A and B (controls). The boxed regions labeled A and B are shown magnified in the right panels. A typical LB and LN are labeled with arrows. Only faint synaptic staining is seen in the normal brain. The same experiment was performed with neo-epitope specific antibody 12C6. The results are shown in FIGS. 18A and B. The boxed regions labeled A and B are shown magnified in the right panels. Typical LB and LNs are labeled with arrows. In panel B, an arrow indicates granular cytoplasmic staining by 12C6. This staining is not seen in normal brain. These results show that the truncated alpha synuclein fragment SN1-119 is enriched in patients with Lewy Body disease.

5. Behavioral Analysis in a Transgenic Animal

For locomotor activity, mice are analyzed for 2 days in the rotarod (San Diego) Instruments, San Diego, Calif.), as previously described (Masliah, et al. (2000)). On the first day mice are trained for 5 trials: the first one at 10 rpm, the second at 20 rpm and the third to fifth at 40 rpm. On the second day, mice are tested for 7 trials at 40 rpm each. Mice are placed individually on the cylinder and the speed of rotation is increased from 0 to 40 rpm over a period of 240 sec. The length of time mice remain on the rod (fall Latency) is recorded and used as a measure of motor function.

Mice are tested for cognitive ability in the Morris Water maze (Morris, Learn Motivat. 12;239-260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues. The length of time the animal remains in the water is inversely related to its cognitive ability.

6. Analysis of Aggregated Alpha-Synuclein Fragments in a Cell Line

GT1-7 neuronal cells (Hsue et al. Am. J. Pathol. 157:401-410 (2000)) are transfected with a pCR3.1-T expression vector (Invitrogen, Carlsbad, Calif.) expressing a truncated fragment of alpha-synuclein as described above murine alpha-synuclein and compared with cells transfected with expression vector alone Cells transfected with vector alone have a fibroblastic appearance while cells transfected with alpha-synuclein are rounded, with inclusion bodies at the cell surface visible via both light and confocal scanning microscopy. Transfected GT1-7 cells can be used to screen agents for activity in clearing synuclein inclusions.

The above examples are illustrative only and do not define the invention; other variants will be readily apparent to those of ordinary skill in the art. The scope of the invention is encompassed by the claims of any patent(s) issuing herefrom. The scope of the invention should, therefore, be determined not with reference to the above description, but

What is claimed is:

1. A method of screening for an agent having a pharmacological activity useful for treating a Lewy Body Disease (LBD) comprising:
contacting the agent with a fragment of alpha synuclein, which is SN1-115, SN1-133 or SN 1-135, with residues-defined by SEQ ID NO:1 or a hereditary variant thereof associated with Lewy body disease, or an induced variant thereof selected from the group consisting of E83Q, A90V and A76T;
determining the rate or extent of aggregation of the alpha synuclein or fragment of alpha-synuclein, wherein a reduction in the rate or extent of aggregation relative to a control lacking the agent indicates the agent has the pharmacological activity.

2. The method of claim 1, wherein the fragment of alpha-synuclein bears a hereditary variant associated with a hereditary LBD.

3. The method of claim 2, wherein the hereditary variant is an A53T mutation, an A30P mutation, an E46K mutation, or any combination thereof.

4. The method of claim 1 wherein the hereditary variant is an A53T mutation.

5. The method of claim 1, further comprising conducting a trial in a human having a LBD or an animal model of LBD to determine whether the agent treats or inhibits a symptom of the LBD.

6. A purified fragment of alpha synuclein, which is SN1-115, SN1-133 or SN 1-135, with residues defined by SEQ ID NO:1 or a hereditary variant thereof associated with Lewy Body disease, or an induced variant thereof selected from the group consisting of E83Q, A90V and A76T.

7. The purified fragment of claim 6, wherein the fragment of alpha-synuclein bears a hereditary variant associated with a hereditary LBD.

8. The fragment of claim 7, wherein the hereditary variant is an A53T mutation, an A30P mutation, an E46K mutation, or any combination thereof.

9. A fragment of alpha synuclein which is SN1-115, SN1-133 or SN 1-135, with residues defined by SEQ ID NO:1, or a hereditary variant thereof associated with Lewy body disease, or a or an induced variant thereof selected from the group consisting of E83Q, A90V and A76T, which fragment is recombinantly expressed or synthesized by solid phase peptide synthesis.

10. The fragment of claim 9, wherein the fragment of alpha-synuclein bears a hereditary variant associated with a hereditary LBD.

11. The fragment of claim 10, wherein the hereditary variant is an A53T mutation, an A30P mutation, an E46K mutation, or any combination thereof.

* * * * *

UNITED STATES PATENT AND TRADEMARK OFFICE
CERTIFICATE OF CORRECTION

| | | |
|---|---|---|
| PATENT NO. | : 7,358,331